US010556886B2

(12) United States Patent
Lee et al.

(10) Patent No.: US 10,556,886 B2
(45) Date of Patent: Feb. 11, 2020

(54) METAL-ORGANIC HYBRID STRUCTURES BUILT WITH MULTI-DIRECTIONAL POLYDENTATE LIGANDS

(71) Applicants: LG CHEM, LTD., Seoul (KR); Seoul National University R&DB Foundation, Seoul (KR)

(72) Inventors: Dongwhan Lee, Seoul (KR); Jung Hwan Kim, Chungcheongbuk-do (KR); Won Jong Kwon, Daejeon (KR); Yong Jin Bae, Daejeon (KR)

(73) Assignees: LG CHEM, LTD., Seoul (KR); Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 16/084,959

(22) PCT Filed: Jul. 28, 2017

(86) PCT No.: PCT/KR2017/008182
§ 371 (c)(1),
(2) Date: Sep. 13, 2018

(87) PCT Pub. No.: WO2018/021882
PCT Pub. Date: Feb. 1, 2018

(65) Prior Publication Data
US 2019/0077788 A1 Mar. 14, 2019

(30) Foreign Application Priority Data
Jul. 29, 2016 (KR) .................. 10-2016-0096905

(51) Int. Cl.
| | |
|---|---|
| *C07D 401/14* | (2006.01) |
| *C07C 251/70* | (2006.01) |
| *C07C 251/86* | (2006.01) |
| *C07D 401/12* | (2006.01) |
| *C07F 1/06* | (2006.01) |
| *C07C 251/24* | (2006.01) |
| *B01J 20/22* | (2006.01) |
| *C07C 251/48* | (2006.01) |
| *C07F 5/00* | (2006.01) |
| *C07F 13/00* | (2006.01) |
| *C07F 15/00* | (2006.01) |
| *C07C 249/04* | (2006.01) |
| *C07C 249/16* | (2006.01) |

(52) U.S. Cl.
CPC .......... *C07D 401/14* (2013.01); *B01J 20/223* (2013.01); *C07C 251/24* (2013.01); *C07C 251/48* (2013.01); *C07C 251/70* (2013.01); *C07C 251/86* (2013.01); *C07D 401/12* (2013.01); *C07F 1/06* (2013.01); *C07F 5/003* (2013.01); *C07F 13/005* (2013.01); *C07F 15/0013* (2013.01); *C07C 249/04* (2013.01); *C07C 249/16* (2013.01)

(58) Field of Classification Search
None
See application file for complete search history.

(56) References Cited

U.S. PATENT DOCUMENTS

| | | | |
|---|---|---|---|
| 4,322,563 | A | 3/1982 | Hoffman |
| 8,362,463 | B2 | 1/2013 | Radu et al. |
| 8,592,626 | B2 | 11/2013 | Inubushi et al. |
| 8,846,212 | B2 | 9/2014 | Lee et al. |
| 2004/0138470 | A1 | 7/2004 | Genet et al. |
| 2007/0185343 | A1 | 8/2007 | Verpoort et al. |
| 2008/0261101 | A1 | 10/2008 | de Figueiredo Gomes et al. |
| 2011/0186835 | A1 | 8/2011 | Herron et al. |

FOREIGN PATENT DOCUMENTS

| | | |
|---|---|---|
| CN | 101391970 | 3/2009 |
| CN | 101392006 | 3/2009 |
| CN | 102503966 | 6/2012 |
| CN | 104557988 | 4/2015 |
| CN | 103102480 | 3/2016 |
| CN | 103396457 | 3/2016 |
| EP | 0509695 | 4/1992 |
| JP | 2004513951 | 5/2004 |
| JP | 4997096 | 8/2012 |
| JP | 5496676 | 5/2014 |
| JP | 2015155397 | 8/2015 |
| KR | 10-2006-0082676 | 7/2006 |
| KR | 10-2007-0104371 | 10/2007 |
| KR | 10-0951765 | 4/2010 |

OTHER PUBLICATIONS

Li et al. "A "turn-on" fluorescent chemosensor for zinc ion with facile synthesis and application in live cell imaging", Analytica Chimica Acta 776 (2013) 69-73 (Year: 2013).*
Sigma-Aldrich MSDS (Year: 2014).*
Asato et al., "First 'Back-to-back' Shaped Compartmental Ligand; Structural Characterization of a Tetranuclear Zinc (II) Complex in a Highly Flattened Form," Chemistry Letters 29(6): 678-679 (2000).
Johansson et al., "Functional Tetrametallic Linker Modules for Coordination Polymers and Metal-Organic Frameworks," Inorg. Chem. 46(6): 2224-2236 (2007).
Che, C. and Huang, J., "Metal complexes of chiral binaphthyl Schiff-base ligands and their application in stereoselective organic transformations," Coordination Chemistry Reviews 242: 97-113 (2003).
Mitra et al., "Self-Exfoliated Guanidinium-Based Ionic Covalent Organic Nanosheets (iCONs)," J. Am. Chem. Soc. 138(8): 2823-2828 (2016).
Xue et al., "Ag(I)-Coordinated Supramolecular Metallogels Based on Schiff Base on Ligands: Structural Characterization and Reversible Thixotropic Property," Cryst. Growth Des 15(11): 5360-5367(A-H) (2015).
Sun et al., "Electrically Conductive Porous Metal-Organic Frameworks," Angew. Chem. Int. Ed. 55: 3566-3579 (2016).

(Continued)

*Primary Examiner* — James W Rogers
(74) *Attorney, Agent, or Firm* — Dentons US LLP

(57) ABSTRACT

A compound represented by Chemical Formula 1 according to the present invention can coordinate with metal ions to form a bidirectional or multidirectional metal-organic hybrid structure. Thus, the present invention can synthesize various ligands using amine-aldehyde condensation, and synthesize metal-organic materials using the same.

7 Claims, 29 Drawing Sheets

(56) References Cited

OTHER PUBLICATIONS

Nishimura et al., "Preparation of metallic BEDT-TTF charge transfer complex of 3,3',5,5'-tetranitro-4,4'-biphenyldiol dianion (TNBP2-) having flexible molecular shape," J. Mater. Chem. 10: 911-919 (2000).
Venkatachalam et al., "Binuclear ruthenium(III) Schiff base complexes bearing N4O4 donors and their catalytic oxidation of alochols," Spectrochimica Acta Part A 71: 884-891 (2008).
Guieu, S., "Synthesis and Characterization of Linear and Macrocyclic Ligands with Multiple Hemisalen Pockets," Synthetic Communications 42: 3177-3186 (2012).
McDonald et al., "Capture of Carbon Dioxide from Air and Flue Gas in the Alkylamine-Appended Metal-Organic Framework mmen-Mg2(dobpdc)," J. Am. Chem. Soc. 134: 7056-7065 (2012).
Golovnia et al., "2,2'-Dihydroxybiphenyl-3,3'-dicarbaldehyde dioxime," Acta Cryst. E65: o2018-o2019 and sup1-sup5 (2009).
Supplementary Search Report of European Patent Office in Appl'n No. EP17834823, dated Mar. 4, 2019.
Yoshihara et al., "Synthesis of Novel Transparent Particles with Alternative Organic-zirconium Hybrid Structures," J. Jpn. Soc. Colour Mater. (Shikizai) 74(5): 229-231 (2001).

\* cited by examiner

METAL-ORGANIC HYBRID STRUCTURES BUILT WITH MULTI-DIRECTIONAL POLYDENTATE LIGANDS

CROSS-REFERENCE TO RELATED APPLICATION

This application is a National Stage Application of International Application No. PCT/KR2017/008182 filed on Jul. 28, 2017, which claims priority to and the benefit of Korean Patent Application No. 10-2016-0096905 filed on Jul. 29, 2016 with the Korean Intellectual Property Office, the disclosures of which are herein incorporated by reference in their entirety for all purposes as if fully set forth herein.

TECHNICAL FIELD

The present invention relates to a multi-directional polydentate ligand for the preparation of a metal-organic hybrid structure and a metal-organic hybrid structure comprising the same.

BACKGROUND OF ART

A Schiff base is formed through the condensation of an amine and an aldehyde. The Schiff base is commonly found in the living system. For example, the amine functional group of a lysine residue of an enzyme intermediate reversibly reacts with a cofactor or substrate. Here, the enzyme cofactor PLP forms a Schiff base with a lysine residue, and is involved in the transaldimidation reaction of a substrate. Through a similar mechanism, a retinal cofactor forms a Schiff base with a lysine residue of rhodopsin.

Further, the Schiff base is one of the representative ligands in coordination chemistry. The nitrogen donor atom has both nucleophilicity and Lewis basicity, and could simultaneously exhibit a 7-acceptor property as well. Representative multidentate ligands based on the Schiff base motif include salen-type ligands. In particular, chiral Schiff bases have been used extensively as ligands for asymmetric catalysis. When the Schiff base is used as the backbone of multidentate ligands to support metal centers of planar coordination geometry, porous network materials can constructed, which have unobstructed channels to facilitate the access of substrates to the metal sites.

A Schiff base involved in 7-conjugation also exhibits various photoelectronic properties. Based on this property, many composite materials having Schiff base functional groups are being used as key electronic components of organic solar cells or perovskite solar cells. Further, covalent organic frameworks (COFs) of Schiff bases are emerging as next-generation molecule-based materials that exploit the reversibility of amine-aldehyde condensation reaction.

To take full advantage of the unique structural, chemical, and photoelectronic properties of the Schiff base, studies for preparing a new framework connected as a two-dimensional or three-dimensional network structure are actively in progress. For example, according to a recently reported document (R. Banerjee et al. *J. Am. Chem. Soc.* 2016, 138, 2823-2828), the aldehyde groups of 1,3,5-triformylphloroglucinol, which is a molecule of $D_{3h}$ symmetry, are condensed with guanidinium having amine groups positioned in three directions to form an ionic covalent organic framework having Schiff base linkages. According to another document (P. Sun et al. *Cryst. Growth. Des.* 2015, 15, 5360-5367), a ligand prepared using Schiff base condensation is reacted with gold to form a metallogel.

The present inventors designed Schiff base-derived multidirectional ligands to maximize the number of metal-ligand bonds, confirmed that metal-organic hybrid structures with network topology are formed through supramolecular interaction with multinuclear repeating units growing bidirectionally, and completed the present invention.

DETAILED DESCRIPTION OF THE INVENTION

Technical Problem

It is an object of the present invention to provide a multi-directional polydentate ligand compound having wide expandability in terms of its structure and functions, for the preparation of a metal-organic hybrid structure.

It is another object of the present invention to provide a metal-organic hybrid structure based on the multi-directional polydentate ligand.

Technical Solution

The present invention provides a metal-organic hybrid structure formed by the coordinate bonding of a compound represented by the following Chemical Formula 1 or a salt thereof with metal ions:

[Chemical Formula 1]

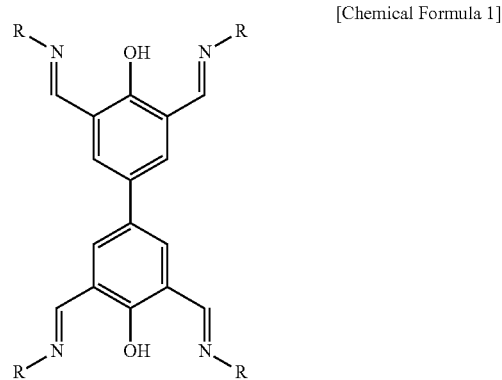

in the Chemical Formula 1,

R's are each independently, —$R^1$, —NH—CO—$R_2$, or —NH—$R_2$, $R_1$'s are each independently, —OH, a $C_{6-60}$ aryl, a $C_{1-10}$ alkyl, or an amino acid residue, and $R_2$'s are a $C_{1-10}$ alkyl, a $C_{6-60}$ aryl, or a $C_{4-60}$ heteroaryl containing one of N, O, and S.

The compound represented by Chemical Formula 1 is a compound for preparing a metal-organic hybrid structure that exhibits porosity, electrical conductivity and electrochromism.

Preferably, $R_1$'s are each independently —OH, phenyl, naphthyl, methyl, ethyl, propyl, isopropyl, butyl, isobutyl, tert-butyl, pentyl, tert-pentyl, neopentyl, isopentyl, sec-pentyl, 3-pentyl, or an amino acid residue selected from the group consisting of alanine, cysteine, aspartic acid, glutamic acid, phenylalanine, histidine, isoleucine, lysine, leucine, methionine, asparagine, pyrrolysine, glutamine, arginine, serine, threonine, selenocysteine, valine, tryptophan, and tyrosine.

The amino acid residue means a structure excluding the amine group in the structure of an amino acid. The amine group condenses with aldehyde to form imine. For example, in the case of alanine, the amino acid residue is propionic acid, which is the structure excluding an amine group in the structure of alanine.

Further, preferably, $R_2$ is methyl, ethyl, propyl, isopropyl, butyl, isobutyl, tert-butyl, pentyl, tert-pentyl, neopentyl, isopentyl, sec-pentyl, 3-pentyl, hexyl, octyl, phenyl, naphthyl, or pyridinyl.

Further, when compound represented by Chemical Formula 1 includes a carboxy group, it may exist in the form of a salt, wherein the counter ion may be $Na^+$, $K^+$, etc.

Representative examples of the compound represented by Chemical Formula 1 include compounds represented by the following Chemical Formulas 1-1 to 1-5:

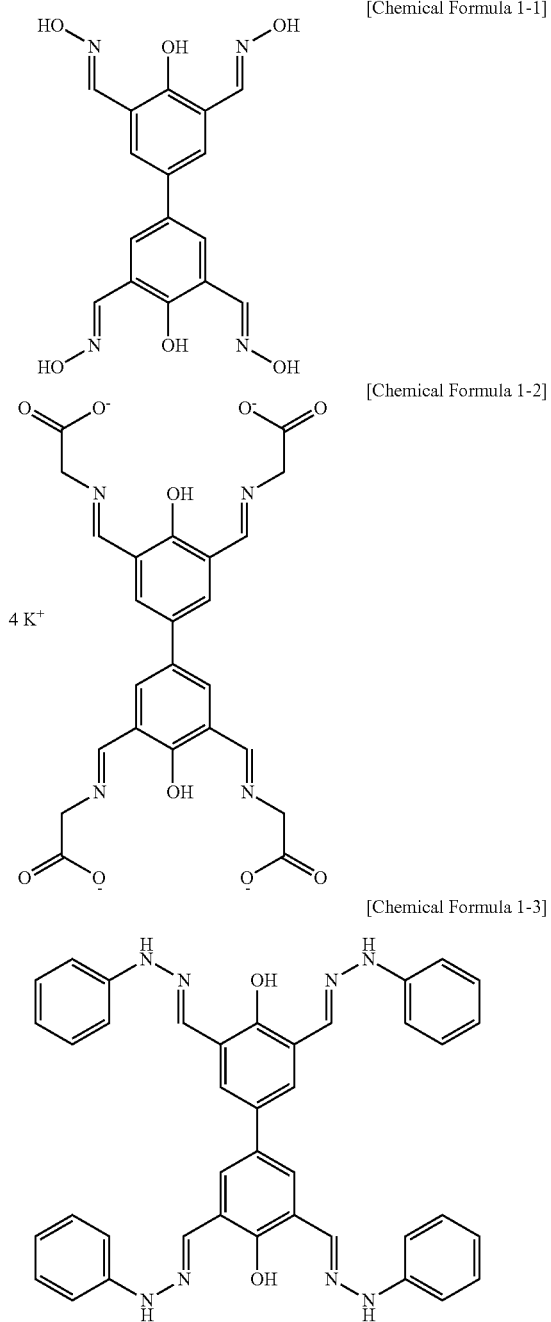

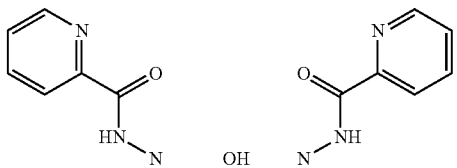

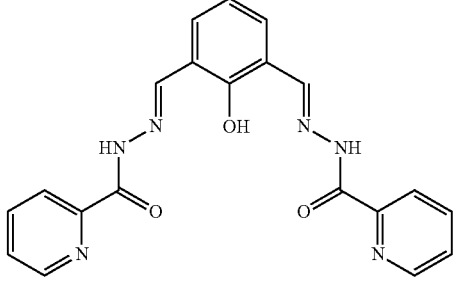

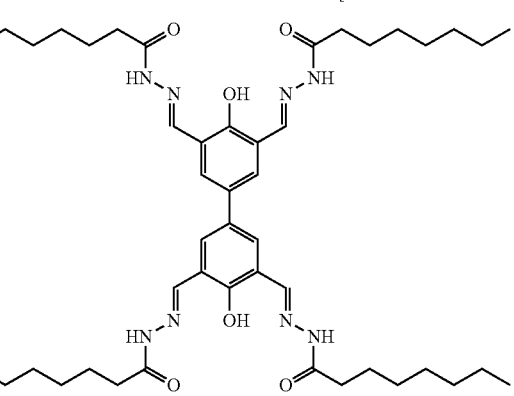

The compound represented by Chemical Formula 1 has a biphenyl scaffold, and it is capable of charge transfer through π-conjugation. Further, the compound represented by Chemical Formula 1 has hydroxy groups on each benzene ring, has two imine groups at the ortho-positions to the hydroxy group. It can coordinate to metal ions through such hydroxy groups and imine groups.

Particularly, the compound represented by Chemical Formula 1 is characterized in that, in addition to the hydroxy groups and imine groups, the substituent R on the imine group may have a $R_1$ substituent, an imide bond (—NH—CO—$R_2$), or an amine group (—NH—$R_2$) that can additionally coordinate with metal ions. Thus, in addition to the coordinate bonds with metal ions through the hydroxy groups and imine groups, additional coordinate bonding with metal ions is possible, and thus, the compound represented by Chemical Formula 1 and metal ions form two-dimensional or three-dimensional network structures. A representative example of the network structure of the metal-organic hybrid structure is shown in FIG. 1.

In the metal-organic hybrid structure of the present invention, the organic ligand of the compound represented by Chemical Formula 1 and metal ions are bonded to form network structures. Among such materials, those having crystallinity are referred to as MOFs (metal-organic frameworks), while those having entrapped solvents without crystallinity are referred to as gel. It is expected that, in such network structure, charge transport is facilitated through the π-conjugation of the biphenol skeleton of the compound represented by Chemical Formula 1 and the coordinated metal ions.

Further, as explained above, the charge transport in the network may be bidirectional or multidirectional rather than unidirectional. Thus, compared to polymers capable of charge transport only through π-conjugation, or polymers capable of unidirectional charge transport, in the metal-organic hybrid structure of the present invention, charge transfer is facilitated, electrical conductivity is remarkably improved, and long distance charge transfer may be expected. In addition, new electrical properties that are difficult to realize with purely organic-based conductive polymers may be expected through the interactions between redox-active transition metal centers that are capable of multi-electron transfer, and redox-active π-conjugated ligands.

The metals of the metal ions are not specifically limited, and for example, may include lanthanide metals such as Tb, Eu, Yb, etc., as well as Period 1 transition metals such as Ti, V, Mn, Fe, Co, Ni, Cu, Zn, etc., Period 2 transition metals such as Zr, Mo, Ru, Rh, Pd, Ag, etc., and Period 3 transition metal such as Ir, Pt, Au, etc.

Further, the metal-organic hybrid structure may be prepared by mixing the above-explained compound represented by Chemical Formula 1 and the precursor of the metal. Here, it is preferable to use a base so that the compound represented by Chemical Formula 1 may be ionized, and for example, an amine (triethylamine), etc. may be used.

The metal-organic hybrid structure in a gel form, according to the present invention, is characterized by the characteristic optical transitions with strong absorptivity in the visible wavelength region, which arise from charge-transfer (CT) electronic transitions. Particularly, it can maintain the gel form even at a high temperature (about 140° C.), which results from the stability of metal-organic network due to the two-dimensional or three-dimensional network structure through the coordinate bond of the compound represented by Chemical Formula 1 and metal ions.

In addition, since this metal-organic hybrid structure includes metal ions, it can be used as a catalyst where such metal ions are used. Particularly, since the metal ions are arranged at a regular interval in the metal-organic hybrid structure, catalytic activity may be further improved. Further, since the optical properties are changed according to the state of the metal ions, it can be applied for various sensors using the same. Moreover, since the metal-organic hybrid structure according to the present invention is porous, it can be applied for gas separation or gas adsorption.

The present invention provides a method for preparing the above-explained compound represented by Chemical Formula 1, as shown in the following Reaction Formula 1.

[Reaction Formula 1]

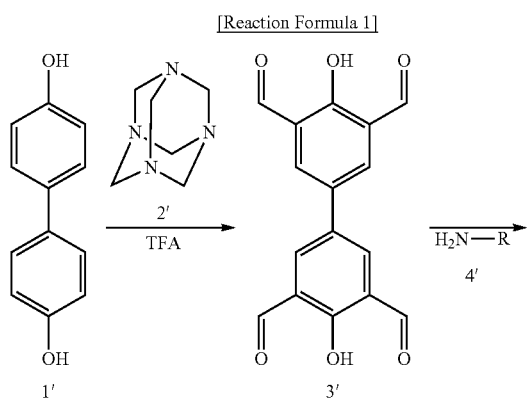

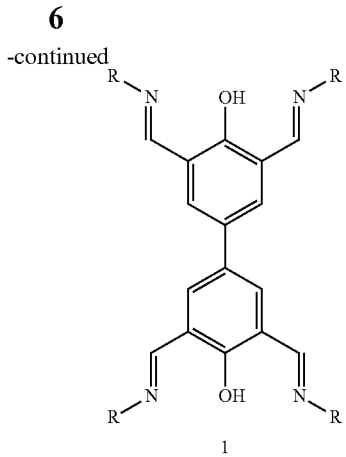

Specifically, the preparation method includes the steps of: reacting a compound represented by Chemical Formula 1', a compound represented by Chemical Formula 2', and trifluoroacetic acid to prepare a compound represented by Chemical Formula 3' (Step 1); and reacting the compound represented by Chemical Formula 3' with a compound represented by Chemical Formula 4' (Step 2).

Step 1 is a Duff reaction, wherein aldehyde groups are substituted at the ortho-positions to the hydroxy groups of the compound represented by Chemical Formula 1'.

Preferably, the mole ratio of the compound represented by Chemical Formula 1' and the compound represented by the Chemical Formula 2' is 1:20. Further, the trifluoroacetic acid also functions as a solvent, and it is preferably used such that it may dissolve both the compound represented by Chemical Formula 1' and the compound represented by Chemical Formula 2'.

Preferably, the reaction temperature of Step 1 is 100° C. to 150° C. Further, preferably, the reaction time of Step 1 is 1 day to 10 days.

After the reaction of Step 1, a step of obtaining the product may be conducted. For example, the reaction mixture may be added to an excess amount (1 mole to 5 moles) of hydrochloric acid, and stirred for 1 day to 3 days to obtain a precipitate. For the purification thereof, the precipitate may be recrystallized with dimethylsulfoxide to obtain a compound represented by Chemical Formula 3'.

Step 2 is the reaction of aldehyde and hydroxyamine to form aldoxime, wherein the aldoxime is formed at the aldehyde group of the compound represented by Chemical Formula 3'. In the compound represented by Chemical Formula 4', R is as defined as in Chemical Formula 1.

As the solvent of the reaction of Step 2, water, a $C_{1-4}$ alcohol, or a mixed solvent thereof may be preferably used, and a water/ethanol mixed solvent or a water/methanol mixed solvent is more preferable.

After the reaction of Step 2, a step of obtaining the product may be conducted. For example, an excess amount of water may be added to filter the produced precipitate, followed by sequentially washing with water and acetone, thus obtaining a compound represented by Chemical Formula 1.

Further, when the compound represented by Chemical Formula 1 is obtained in the form of a gel, it may be treated with supercritical carbon dioxide to remove the solvent, as necessary.

Advantageous Effects

As explained above, the compound represented by Chemical Formula 1 according to the present invention can coordinate with metal ions to form a bidirectional or multidirectional metal-organic hybrid structure. Thus, the present invention can provide a precursor capable of synthesizing various ligands using amine-aldehyde condensation, and use the precursor for the synthesis of metal-organic materials.

DETAILED DESCRIPTION OF THE EMBODIMENTS

Figure 1:
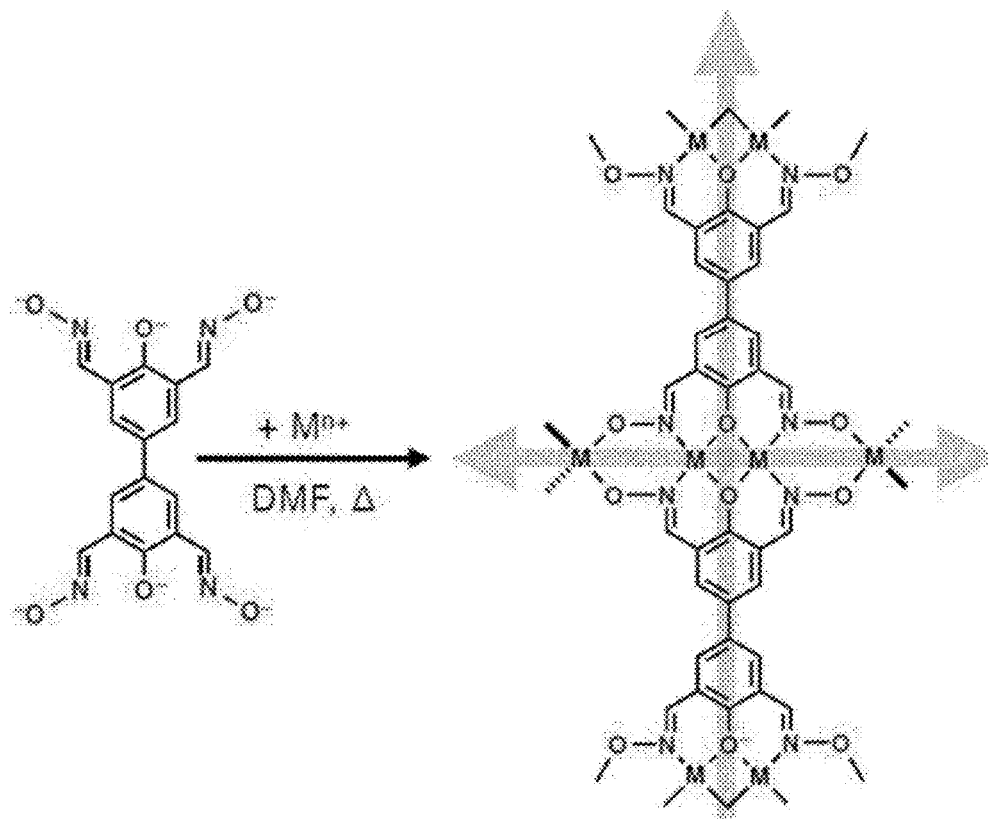
FIG. 1 shows the network structure formed by the coordination bond of the compound according to one embodiment of the present invention with metal ions.

Hereinafter, preferable examples are presented for better understanding of the present invention. However, these examples are presented only as illustrations of the present invention, and the scope of the present invention is not limited thereby.

Example 1

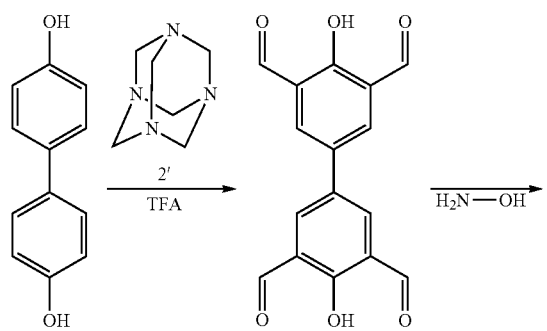

-continued

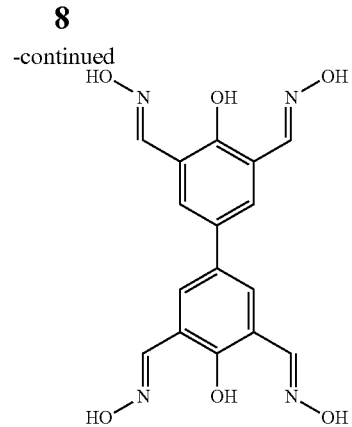

(Step 1)

HMTA (hexamethylenetetramine, 7.530 g, 53.70 mmol) was added into a dried round-bottom flask. The flask was purged with argon, and TFA (trifluoroacetic acid, 50 mL) was added. After completely dissolving HMTA, biphenyl-4,4'-diol (1.000 g, 5.370 mmol) was rapidly added. After confirming that the mixture turned to an orange color, the mixture was heated at 120° C. for 7 days. The product was dark red, and it was poured into 4 N HCl (100 mL) to isolate the yellow precipitate. The precipitate was recrystallized with hot DMSO to obtain 2.460 g of yellow microcrystals (yield: 65.1%).

(Step 2)

The compound (0.296 g, 1.000 mmol) prepared in Step 1 and NH$_2$OH—HCl (0.420 g, 6.0 mmol) were added into a reactor. After adding water (7 mL), the mixture was heated to 80° C. Methanol was added dropwise until the mixture became transparent. After tightly sealing the reactor, the mixture was heated to 100° C. for 1 hour. After cooling to room temperature, water was added to induce precipitation. The solid material was isolated by filtration, and washed with water to obtain a light yellow product (powder, 0.360 g).

$^1$H NMR (300 MHz, DMSO-d) δ 11.60 (s, 4H), 10.88 (s, 2H), 8.45 (s, 4H), 7.83 (s, 4H)

Example 2

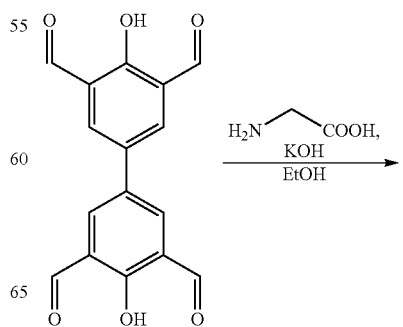

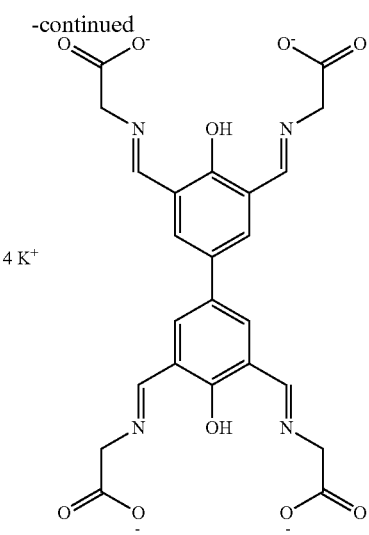

Potassium hydroxide (6.80 mmol, 0.38 g) and 10 mL of ethanol were added into a reactor and stirred. Glycine (6.80 mmol, 0.510 g) was added to the mixture with stirring, and the mixture was stirred until solid materials were completely dissolved. A mixture in which tetraformylbiphenol (1.70 mmol, 0.500 g) prepared in Step 1 of Example 1 was dispersed in 10 mL of ethanol was separately prepared, and then it was slowly added to the reactor with stirring. During the addition, the mixture turned red. After the addition was finished, the mixture was poured into 20 mL of water, and then non-dissolved solid materials were removed by filtration. After removing water under reduced pressure, the remaining material was dispersed in a solvent of dimethylformamide and filtered to obtain a product in the form of an orange powder (0.4654 g, 74.6%).

$^1$H NMR (300 MHz, D2O) δ 3.31 (s, 8H), 7.91 (s, 4H)

Example 3

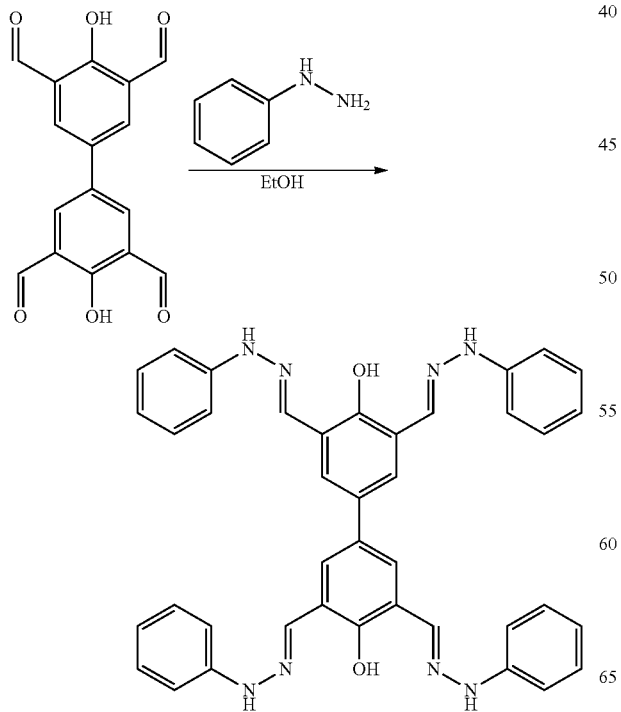

13 mL of ethanol was added into a reactor containing tetraformylbiphenol (0.500 g, 1.678 mmol) prepared in Step 1 of Example 1. While stirring the mixture, phenyl hydrazine (0.726 g, 6.710 mmol) was added with a syringe. The reactor was sealed and heated at 100° C. for 8 hours. The reaction mixture was cooled to room temperature, and then poured into 100 mL of water. The resulting precipitate was isolated by filtration, and washed with acetone to obtain a product in the form of a yellow powder (0.7797 g, 70.6%).

LC-MS: calculated for $C_{40}H_{34}N_8O_2$ [M]$^+$ 658.28, found 659.4.

Example 4

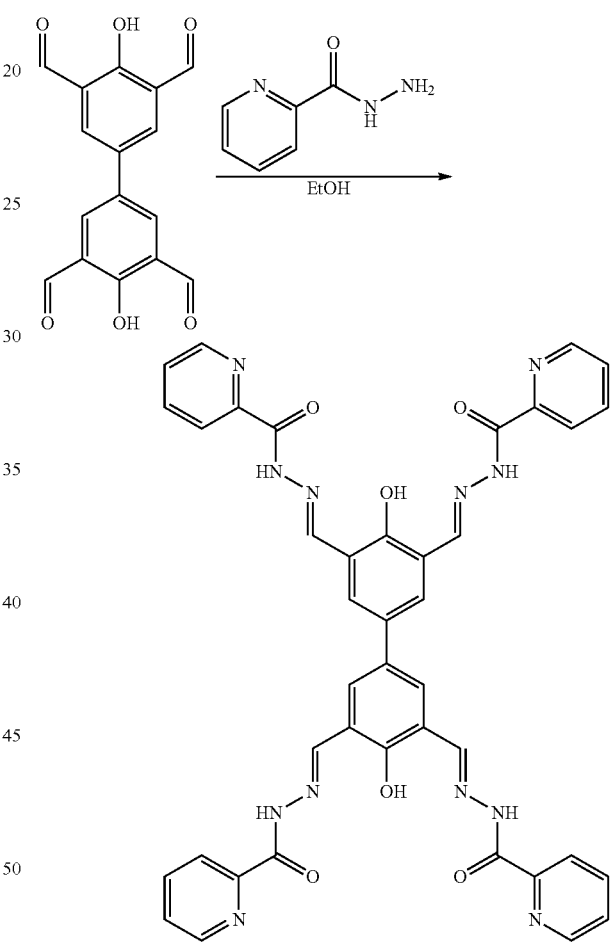

Tetraformylbiphenol (0.500 g, 1.678 mmol) prepared in Step 1 of Example 1 and nicotinic hydrazide (0.920 g, 6.710 mmol) were added into a reactor, and 13 mL of ethanol was added thereto. The reactor was sealed and heated at 100° C. for 8 hours. The reaction mixture was cooled to room temperature, and then poured into 100 mL of water. The precipitate was isolated by filtration, and washed with acetone to obtain the product in the form of a yellow powder (0.8971 g, 69.1%).

MALDI-TOF: calculated for $C_{40}H_{30}N_{12}O_6$ [M]$^+$ 774.24, found 775.5.

Example 5

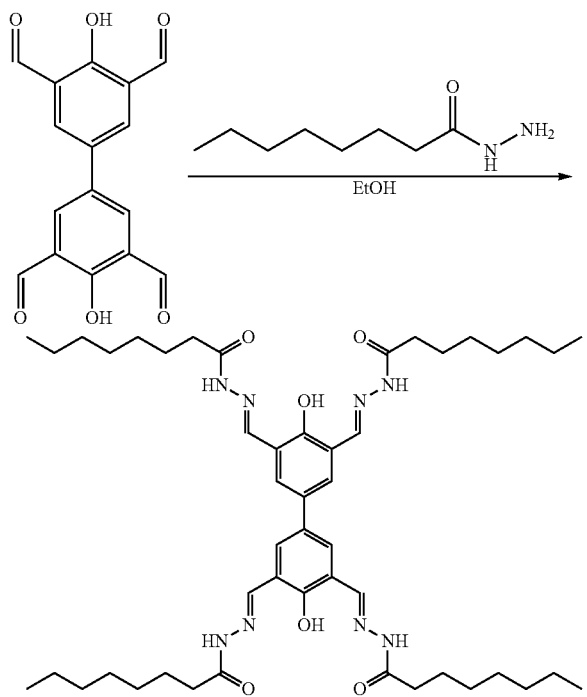

Tetraformylbiphenol (0.500 g, 1.678 mmol) prepared in Step 1 of Example 1 and n-octanohydrazide (1.062 g, 6.710 mmol) were added into a reactor, and 13 mL of ethanol was added thereto. The reactor was sealed and heated at 100° C. for 8 hours. The reaction mixture was cooled to room temperature, and then poured into 100 mL of water. The precipitate was isolated by filtration, and washed with acetone to obtain a product in the form of a yellow powder (0.8072 g, 56.0%).

LC-MS: calculated for $C_{48}H_{74}N_8O_6$ [M]+ 858.57, found 859.7.

Experimental Example 1: Preparation of Gel

1) Experimental Example 1-1

The compound prepared in Example 1 (50.0 mg, 0.140 mmol) was added into a vial, and DMF (1.0 mL) was added to dissolve it. After adding triethylamine (0.12 mL, 0.840 mmol) dropwise and confirming that the solution turned to an orange color, the material of the following Table 1 was rapidly added. After stirring the mixture for 5 seconds, it was heated to 100° C. to form a gel, during which time the gel was gradually formed.

TABLE 1

| | |
|---|---|
| Experimental Example 1-1 | $Mn(OAc)_2 \cdot 4H_2O$ (90.0 mg, 0.240 mmol) dissolved in DMF (3.0 mL) |

2) Experimental Example 1-2

The compound prepared in Example 1 (50.0 mg, 0.140 mmol) was added into a vial, and DMF (1.0 mL) was added to dissolve it. After it was completely dissolved, the material of the following Table 2 was added. Thereafter, triethylamine (0.12 mL, 0.840 mmol) was rapidly added dropwise, and immediately after the addition, a black gel was formed. After stirring the mixture for 5 seconds, it was heated to 100° C. for homogenization of a gel and an increase in the strength thereof. After about 1 hour, the gelation process was completed.

TABLE 2

| | |
|---|---|
| Experimental Example 1-2 | $FeCl_2$ (90.0 mg, 0.240 mmol) dissolved in DMF (3.0 mL) |

3) Experimental Examples 1-3 to 1-6

The compound prepared in Example 1 (50.0 mg, 0.140 mmol) was added into a vial, and DMF (1.0 mL) was put therein to dissolve it. After adding triethylamine (0.12 mL, 0.840 mmol) dropwise and confirming that the solution turned to an orange color, the materials of the following Table 3 were rapidly added. Immediately after the addition, a gel began to form. After stirring the mixture for 5 seconds, it was heated to 100° C. for the homogenization of the gel and an increase in the strength thereof. After about 1 hour, the gelation process was completed.

TABLE 3

| | |
|---|---|
| Experimental Example 1-3 | $CO(OAc)_2 \cdot 4H_2O$ (90.0 mg, 0.280 mmol) dissolved in DMF (3.0 mL) |
| Experimental Example 1-4 | $Ni(OAc)_2 \cdot 4H_2O$ (140.0 mg, 0.420 mmol) dissolved in DMF (3.0 mL) |
| Experimental Example 1-5 | $Cu(OAc)_2 \cdot H_2O$ (140.0 mg, 0.420 mmol) dissolved in DMF (3.0 mL) |
| Experimental Example 1-6 | $Zn(OAc)_2 \cdot 2H_2O$ (140.0 mg, 0.420 mmol) dissolved in DMF (3.0 mL) |

Figure 2:
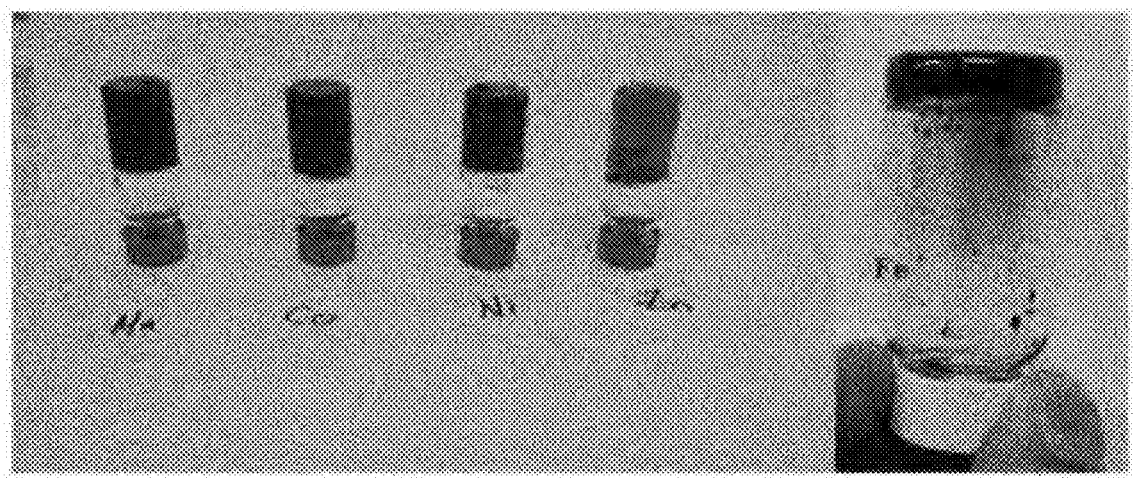
FIG. 2 shows that the metal-organic hybrid structure of the present invention is prepared in the form of gel.

Each gel prepared in Experimental Examples 1-1, 1-3, 1-4, and 1-6 are shown in FIG. 2. As shown in FIG. 2, each metal-organic hybrid structure was prepared in the form of a gel.

4) Experimental Examples 1-7 to 1-10

The compound prepared in Example 1 (50.0 mg, 0.140 mmol) was added into a vial, and DMF (1.0 mL) was added to dissolve it. After adding a solution of sodium methoxide (22.5 mL, 0.420 mmol) in 1.0 mL of ethanol dropwise and confirming that the solution turned to an orange color, the materials of the following Table 4 were rapidly added. Immediately after the addition, a gel began to form. After stirring the mixture for 5 seconds, it was heated to 100° C. for the homogenization of the gel and an increase in the strength thereof. After about 1 hour, the gelation process was completed.

TABLE 4

| | |
|---|---|
| Experimental Example 1-7 | $Pd(OAc)_2$ (95.0 mg, 0.420 mmol) dissolved in DMF (3.0 mL) |
| Experimental Example 1-8 | $Ru(acac)_3$ (113.0 mg, 0.280 mmol) dissolved in DMF (3.0 mL) |
| Experimental Example 1-9 | $Tb(NO_3)_3 \cdot 5H_2O$ (122.0 mg, 0.280 mmol) dissolved in DMF (3.0 mL) |
| Experimental Example 1-10 | $Eu(NO_3)_3 \cdot 5H_2O$ (119.0 mg, 0.280 mmol) dissolved in DMF (3.0 mL) |

Experimental Example 2: Measurement of Fluorescence of Gel

Figure 3:
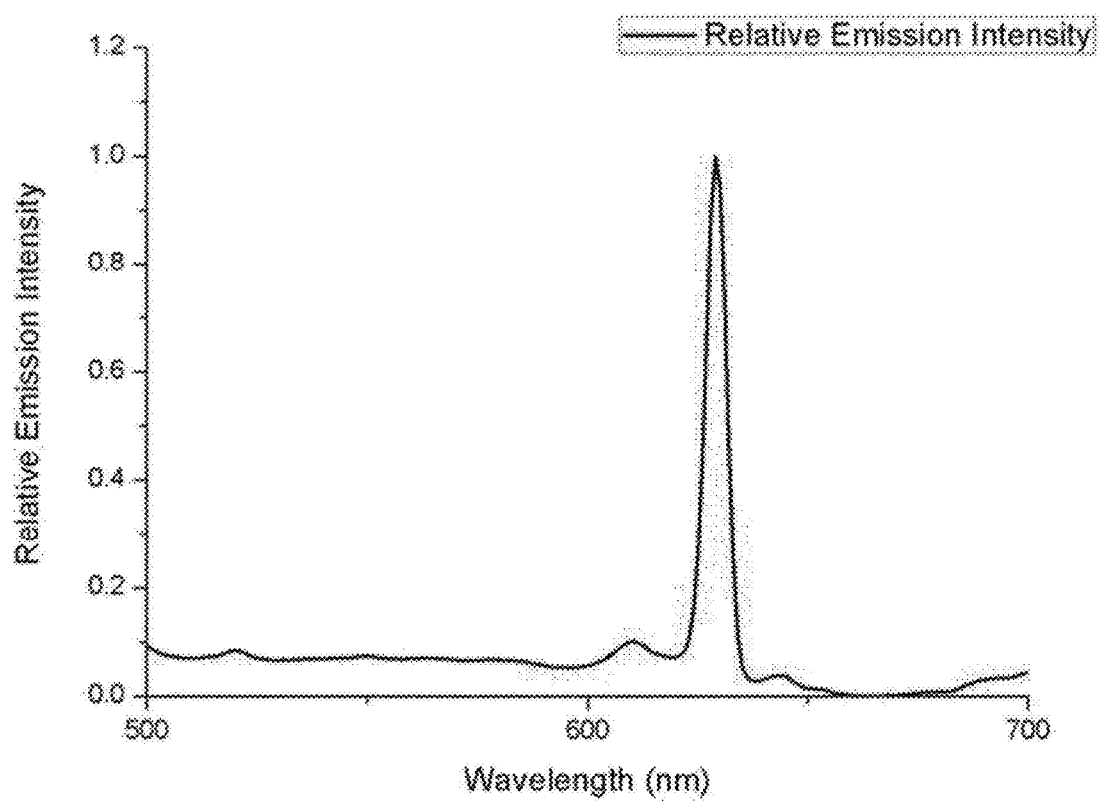
FIG. 3 shows the result of measuring fluorescence of the metal-organic hybrid structure of the present invention (terbium(III) metallogel) (solid fluorescence, absorption wavelength=450 nm, maximum emission wavelength=629 nm, baseline corrected).

The gel prepared in Experimental Example 1-9 was applied on a slide glass, and then dried in a vacuum oven at 80° C. for 2 hours. The fluorescence spectrum of the dried gel was measured, an excitation wavelength was 450 nm, and a maximum emission wavelength was 629 nm as shown in FIG. 3.

Experimental Example 3: Observation of the SEM Image of the Gel

1) Experimental Example 3-1

Figure 4:
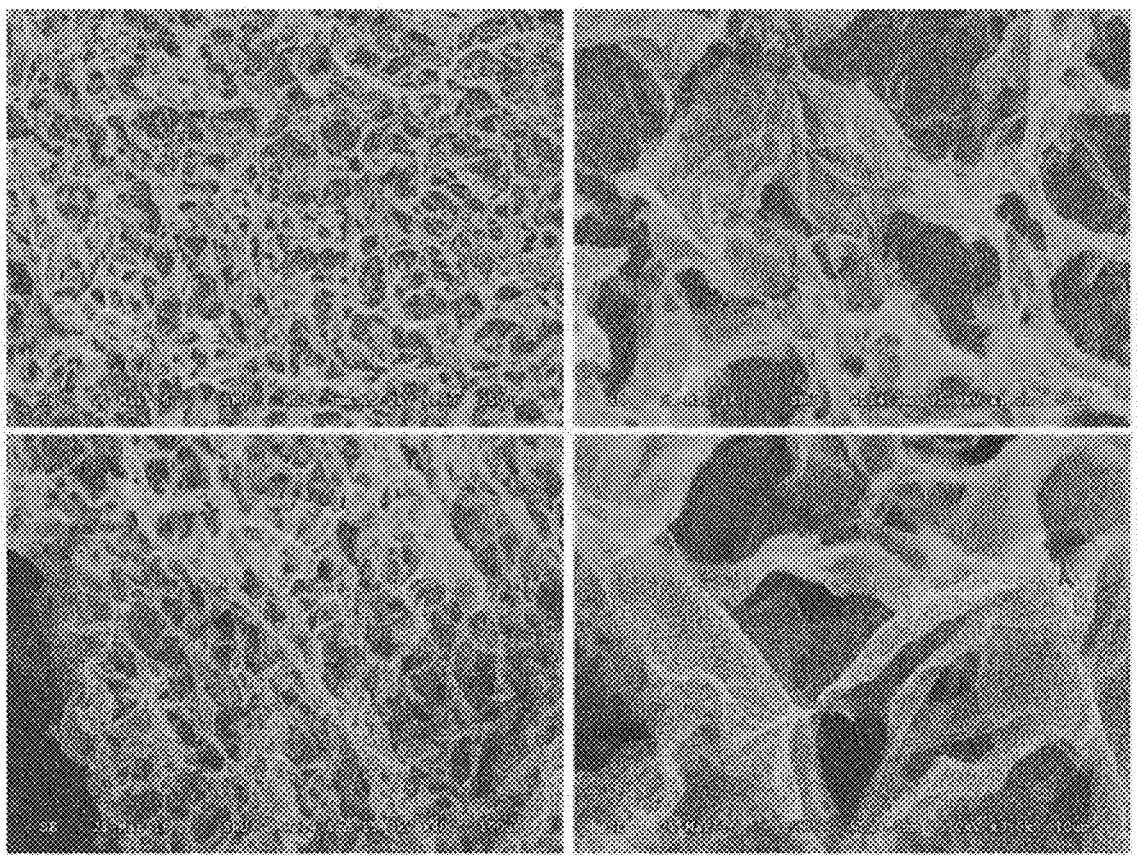
FIG. 4 shows the result of observing the surface of the metal-organic hybrid structure of the present invention (cobalt(II) metallogel) with SEM.

A cobalt gel prepared in Experimental Example 1-3 was dried under vacuum for 12 hours, and a SEM image was obtained using the product. Specifically, the dried gel was dispersed in a stub, to which a carbon double-sided tape was attached, and coated with platinum, and it was observed under a 15 kV voltage condition. The result is shown in FIG. 4.

2) Experimental Example 3-2

Figure 5:
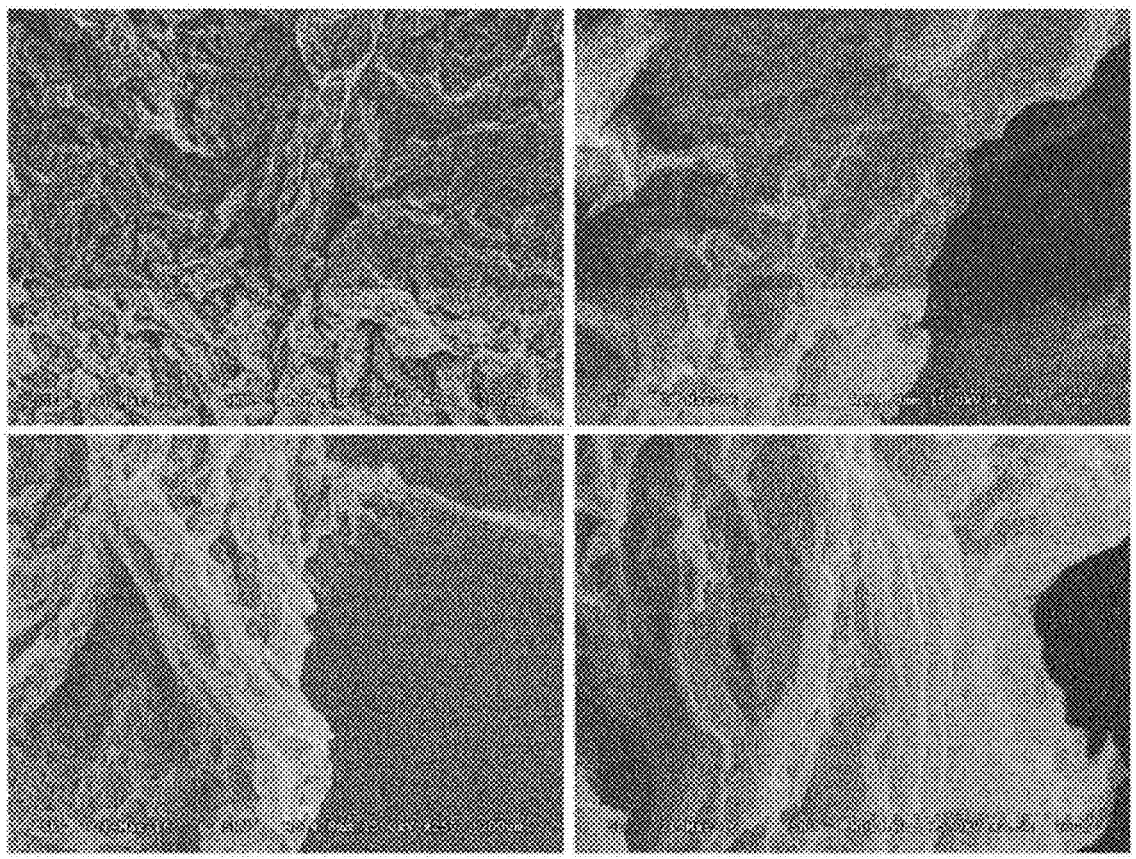
FIG. 5 shows the result of observing the surface of the metal-organic hybrid structure of the present invention (nickel(II) metallogel) with SEM.

A nickel gel prepared in Experimental Example 1-4 was dried under vacuum for 12 hours, and a SEM image was obtained using the product. Specifically, the dried gel was dispersed in a stub, to which a carbon double-sided tape was attached, and coated with platinum, and it was observed under a 5-15 kV voltage condition. The result is shown in FIG. 5.

Experimental Example 4: Preparation of Xerogel

Figure 6:
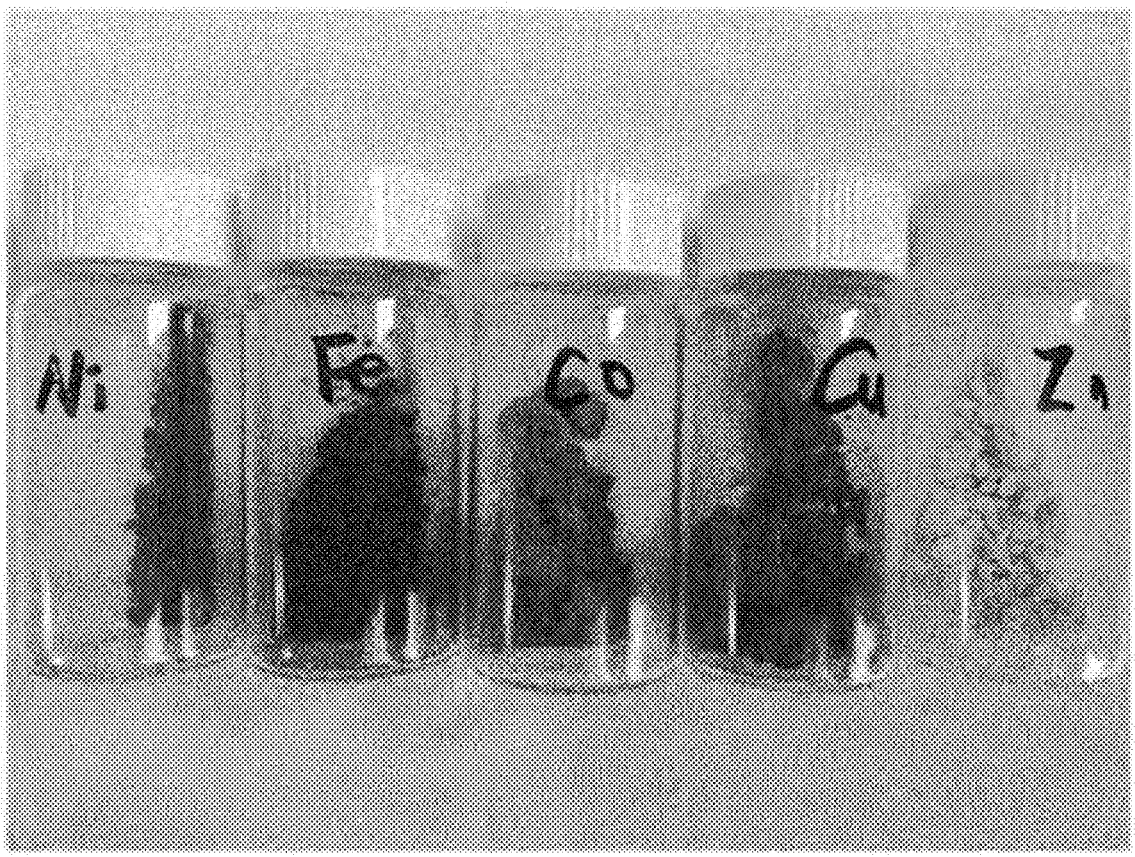
FIG. 6 shows the result of preparing the metal-organic hybrid structure of the present invention as a xerogel.

The gels prepared in Experimental Examples 1-2 to 1-10 were treated with supercritical carbon dioxide to remove the solvent, thus preparing xerogels. Specifically, the above prepared gel was loaded into a cylinder made of stainless steel, and then it was installed inside a supercritical carbon dioxide apparatus. At 40° C., 200 atm of supercritical carbon dioxide was flowed at a rate of 0.1 mL/minute to remove the solvent, thus obtaining a product in the form of a powder. The results of observing a part of them with the unaided eyes are shown in FIG. 6.

Experimental Example 5: Analysis of Xerogel

Using the xerogel prepared in Experimental Example 4, a SEM image was obtained. Specifically, the xerogel was dispersed in a stub, to which a carbon double-sided tape was attached, coated with platinum, and it was observed under a 5-15 kV voltage condition, and the results are shown in FIGS. 7-15. Simultaneously, the element distribution of the xerogel surface was measured by EDS (energy dispersive X-ray spectroscopy), and the results are shown in FIGS. 16a-23b. The contents of each drawing are as described in the following Table. 5.

TABLE 5

Figure 7:
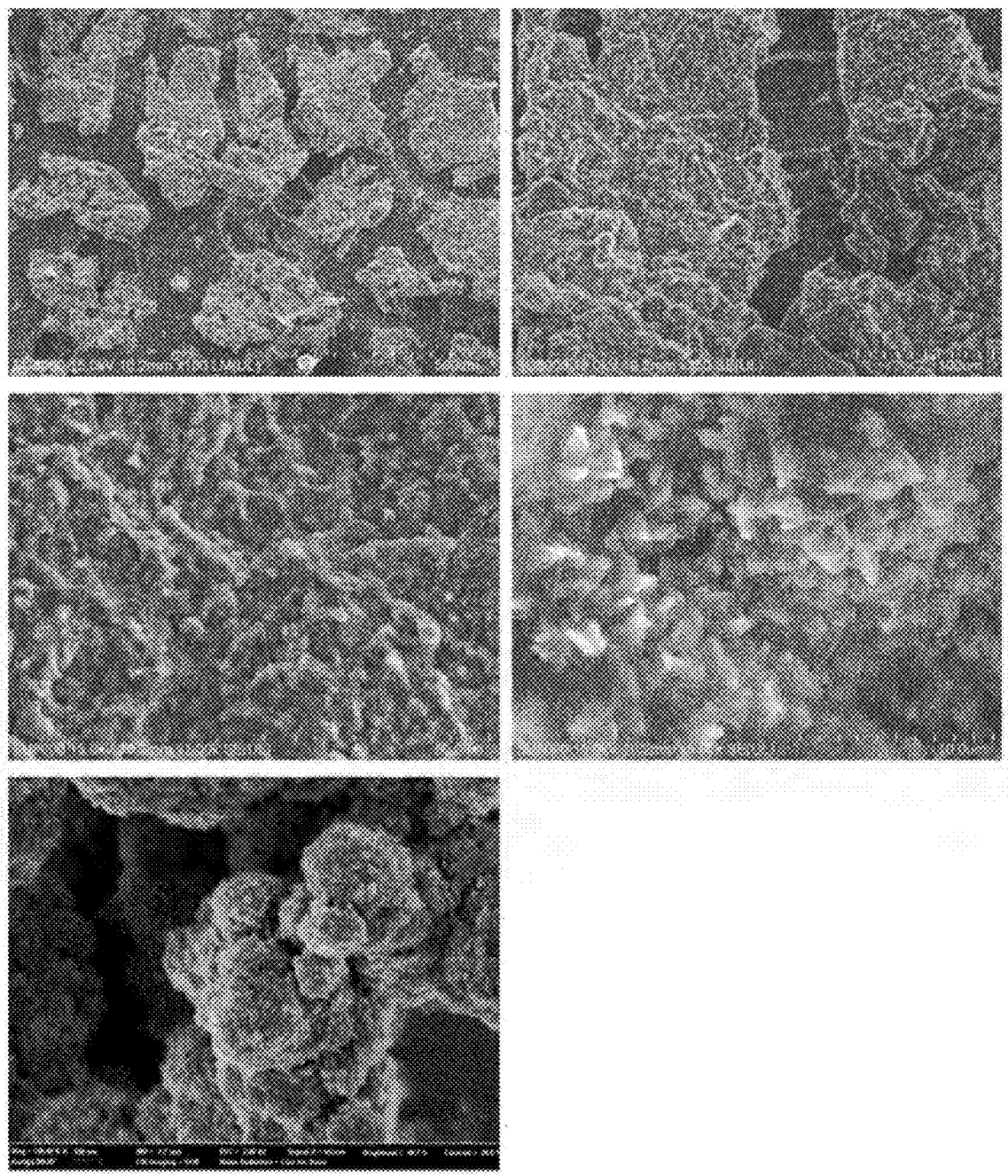
FIGS. 7 to 14 show the results of preparing the metal-organic hybrid structure of the present invention as a xerogel, and observing the surfaces with SEM.
Figure 8:
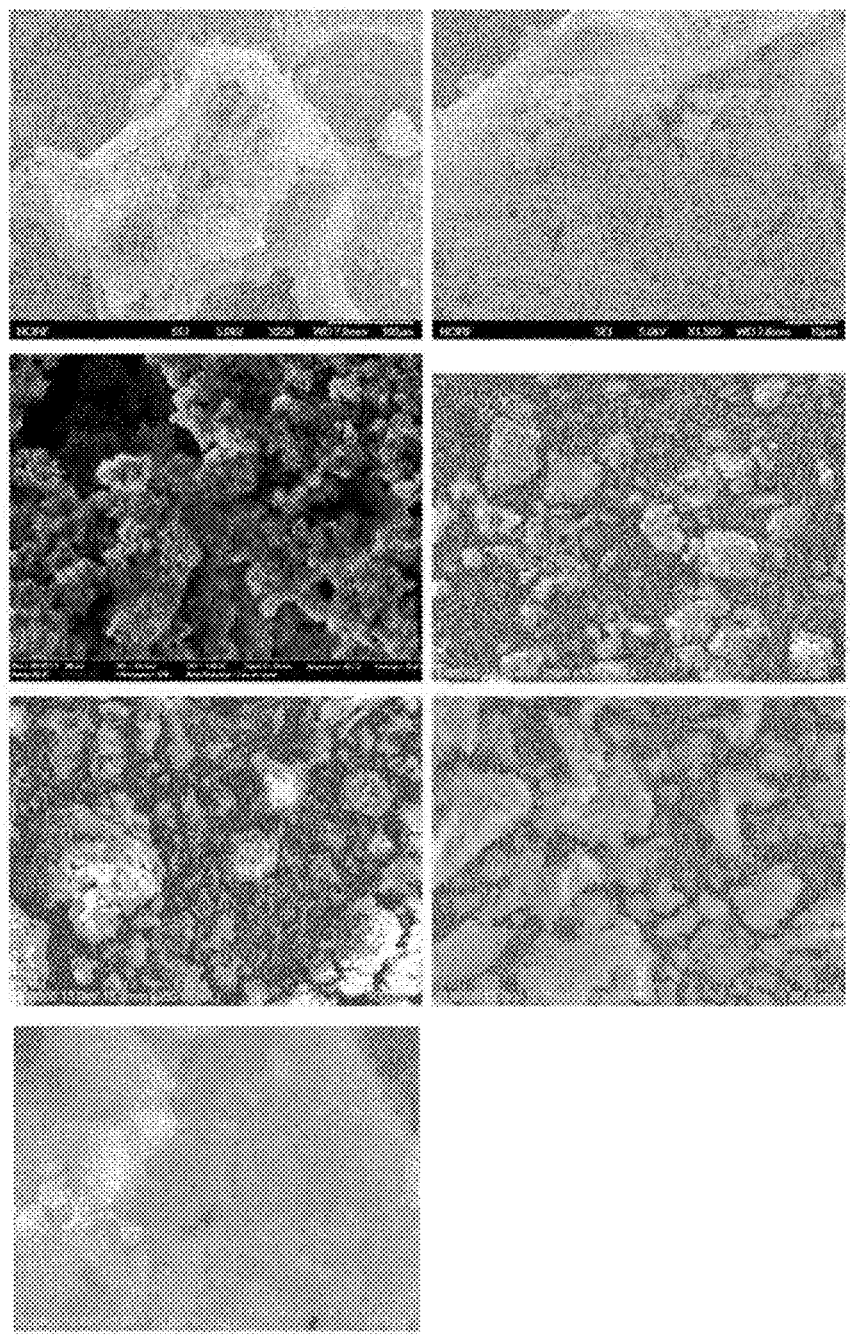
Figure 9:
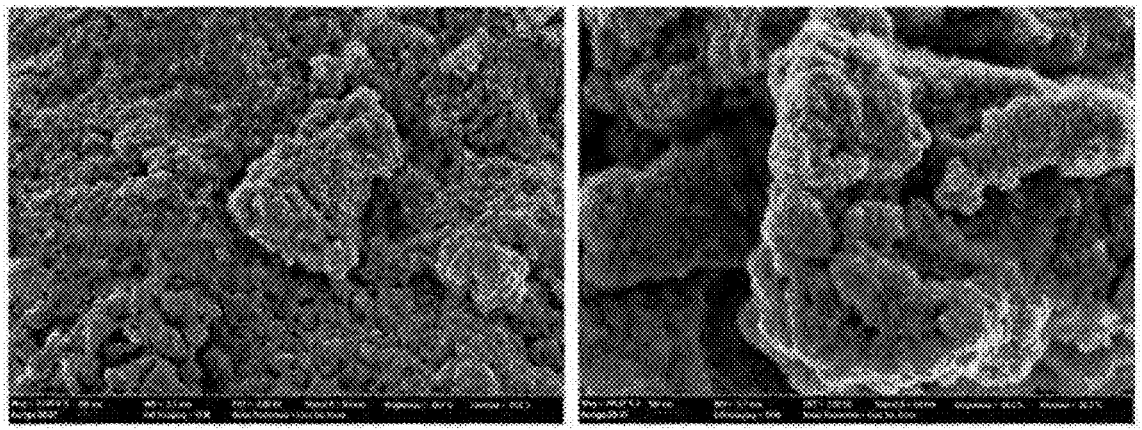
Figure 10:
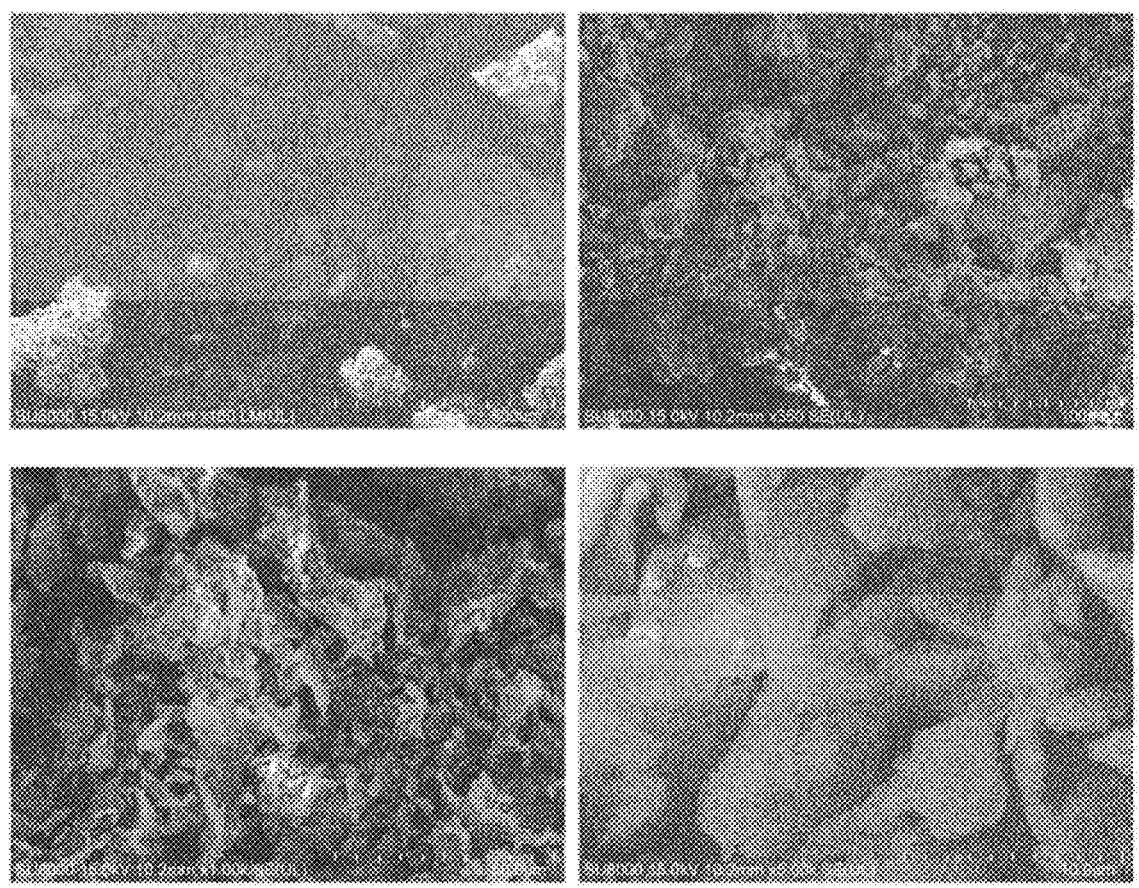
Figure 11:
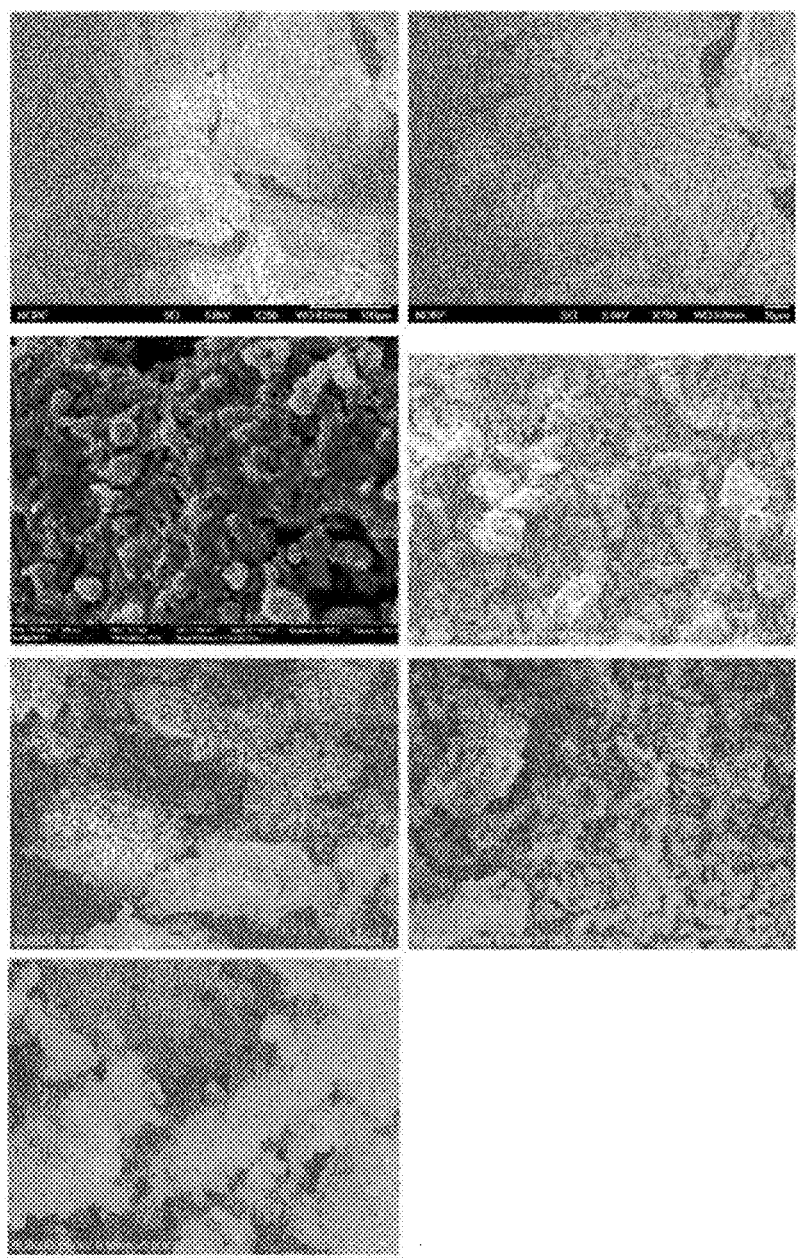
Figure 12:
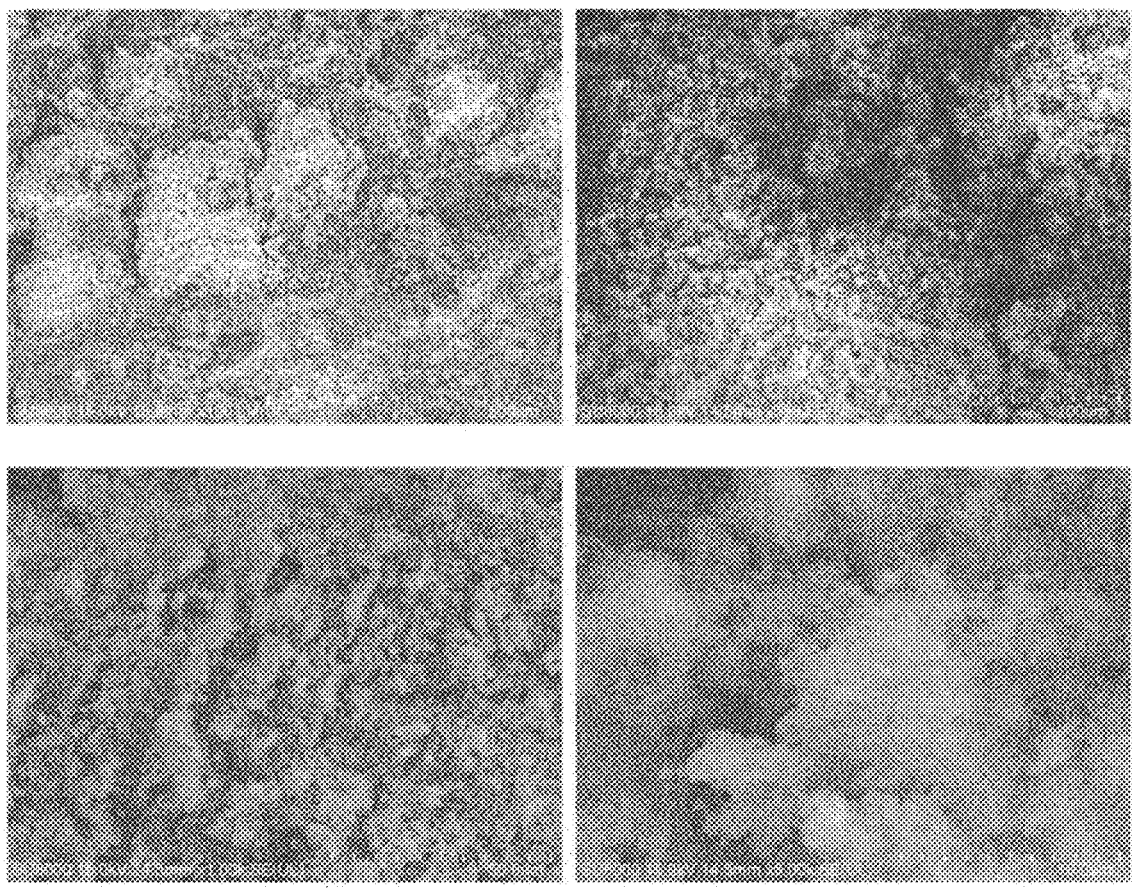
Figure 13:
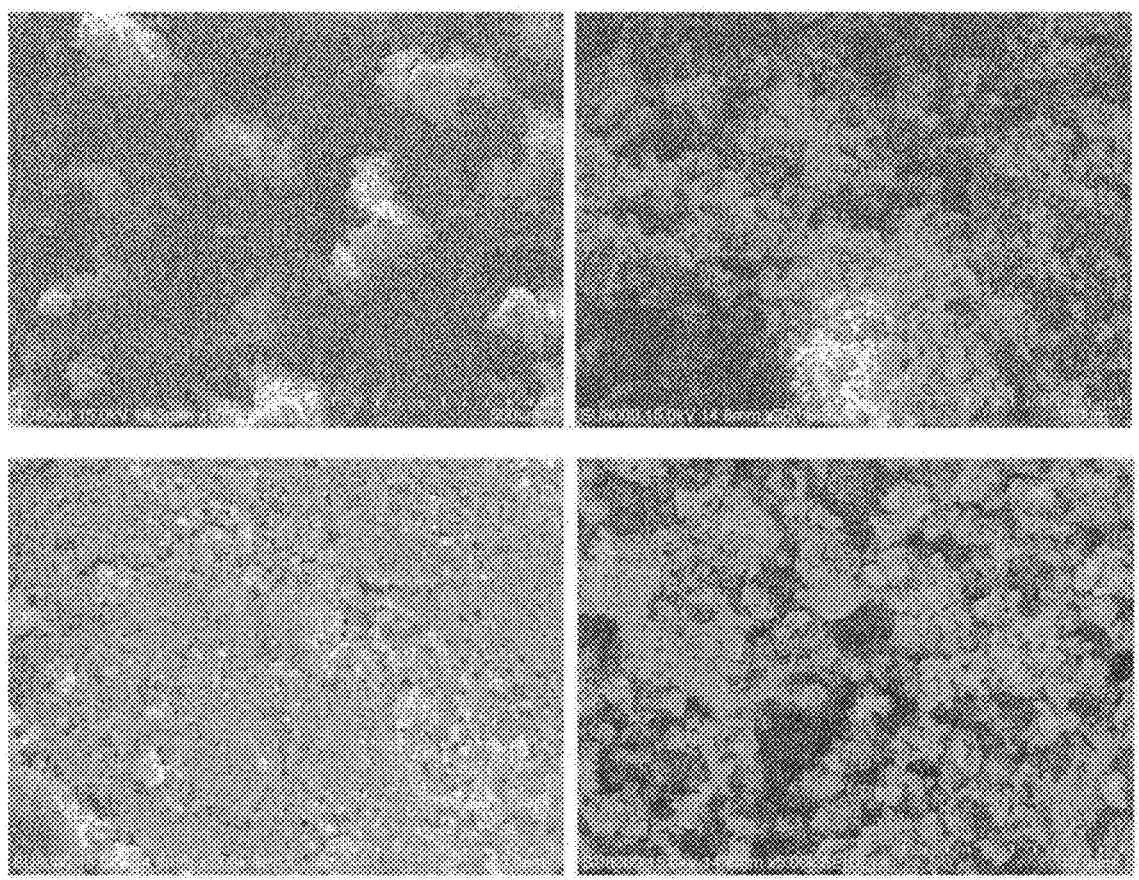
Figure 14:
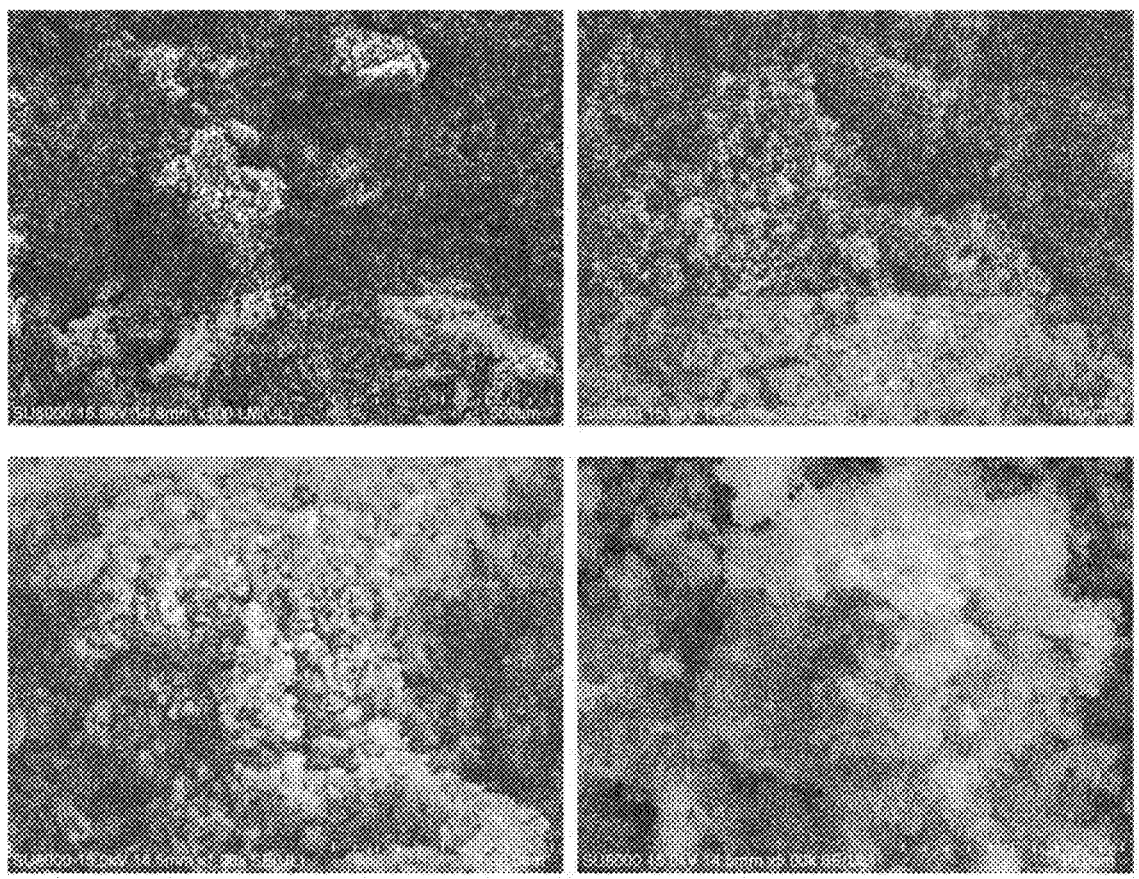
Figure 15:
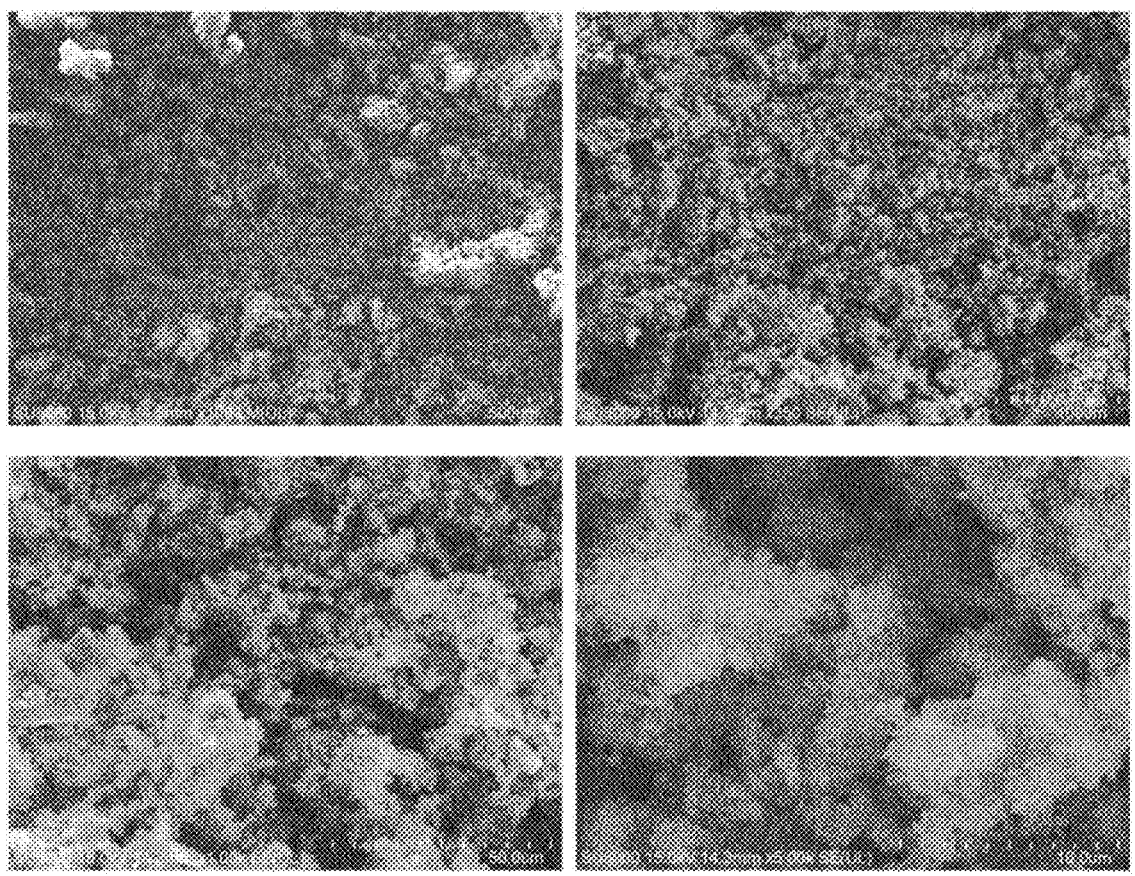
FIGS. 15 to 23b show the results of preparing the metal-organic hybrid structure of the present invention as a xerogel, and observing the content of each element and the distribution in the sample with EDS (energy dispersive X-ray spectrometry).
Figure 16A:
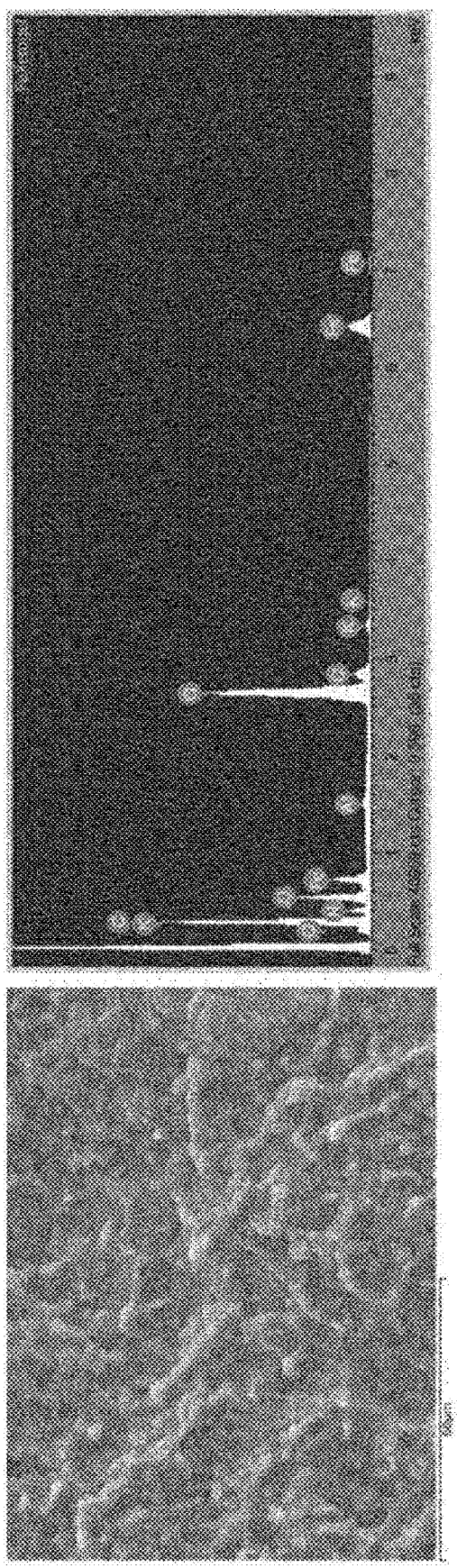
Figure 16B:
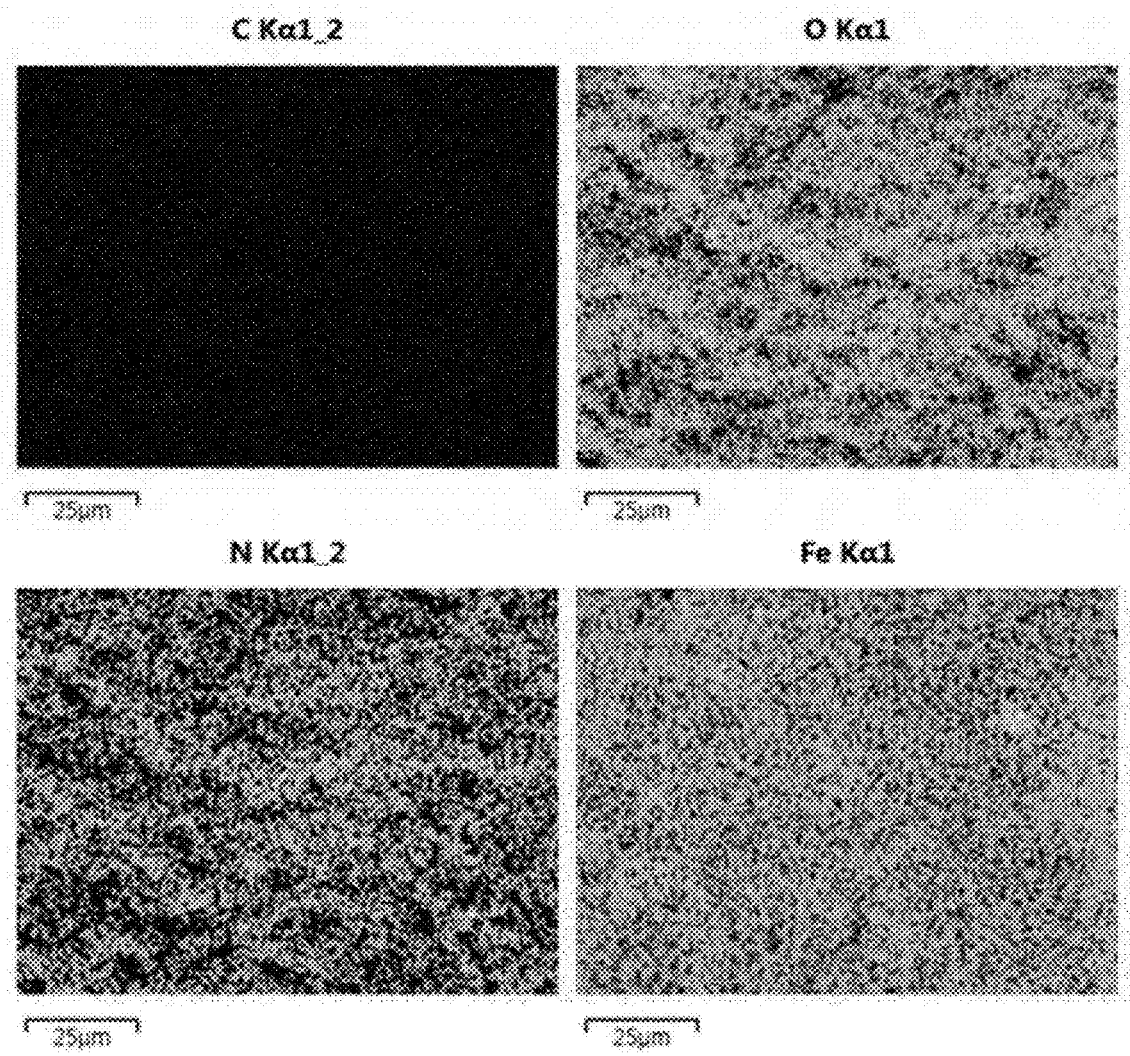
Figure 17A:
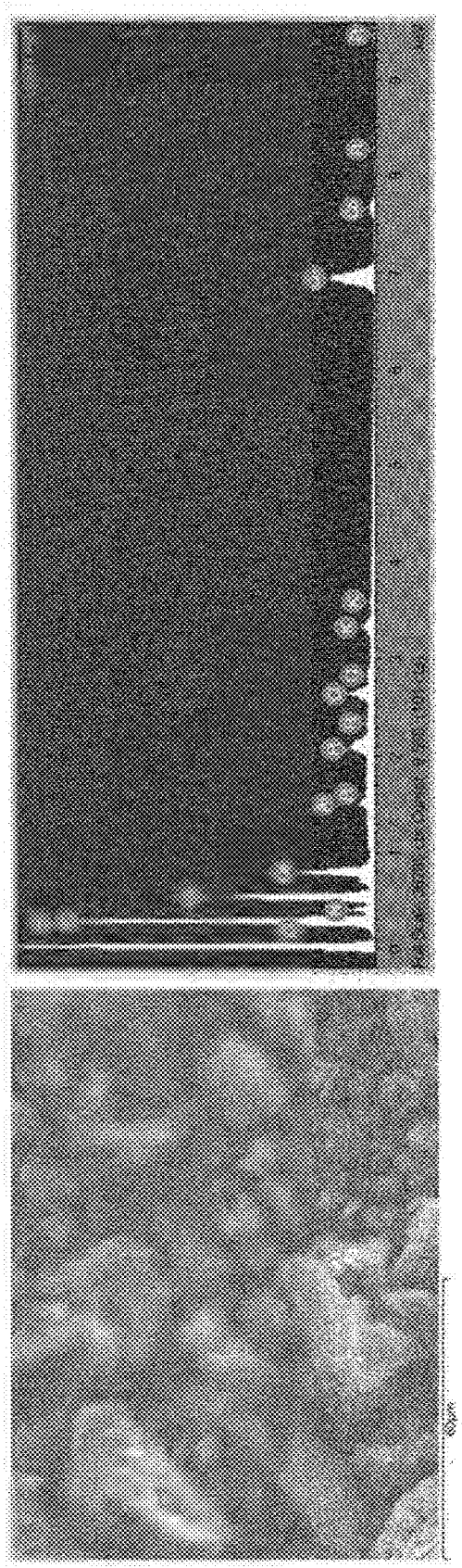
Figure 17B:
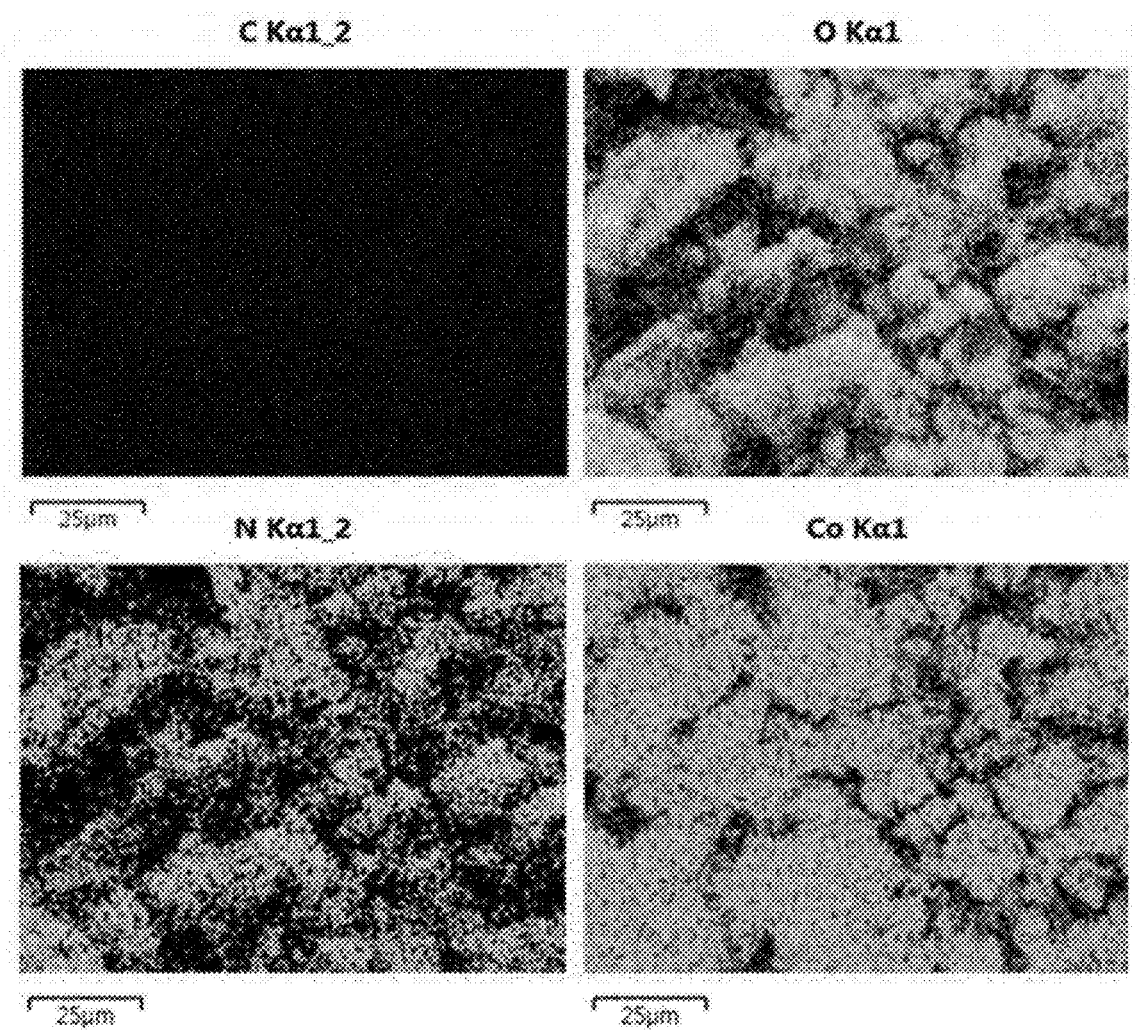
Figure 18A:
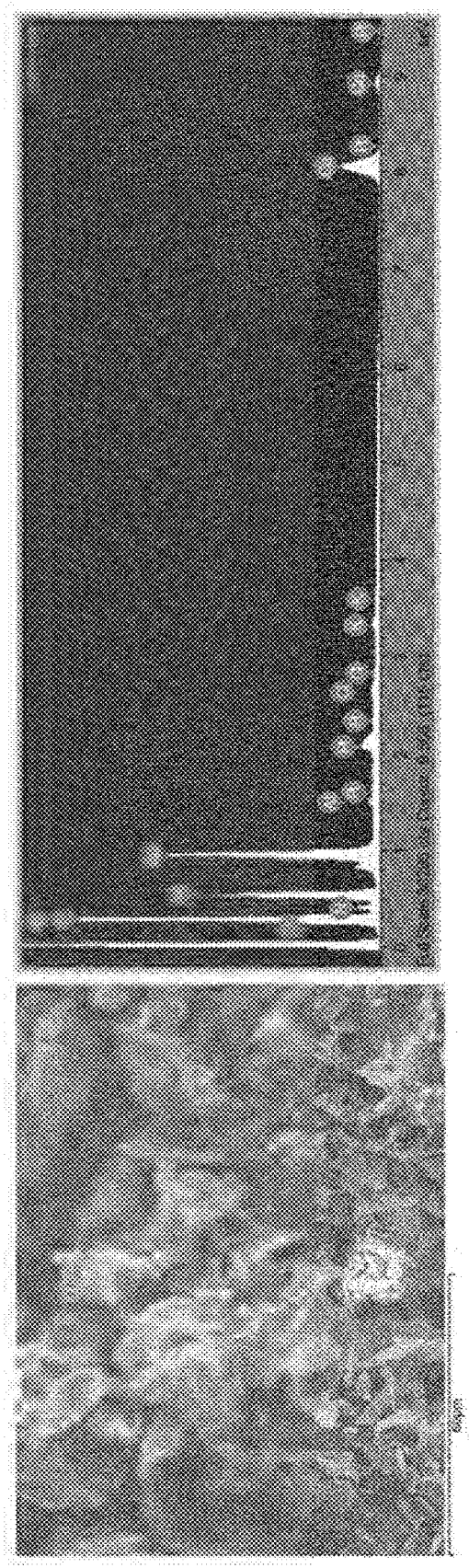
Figure 18B:
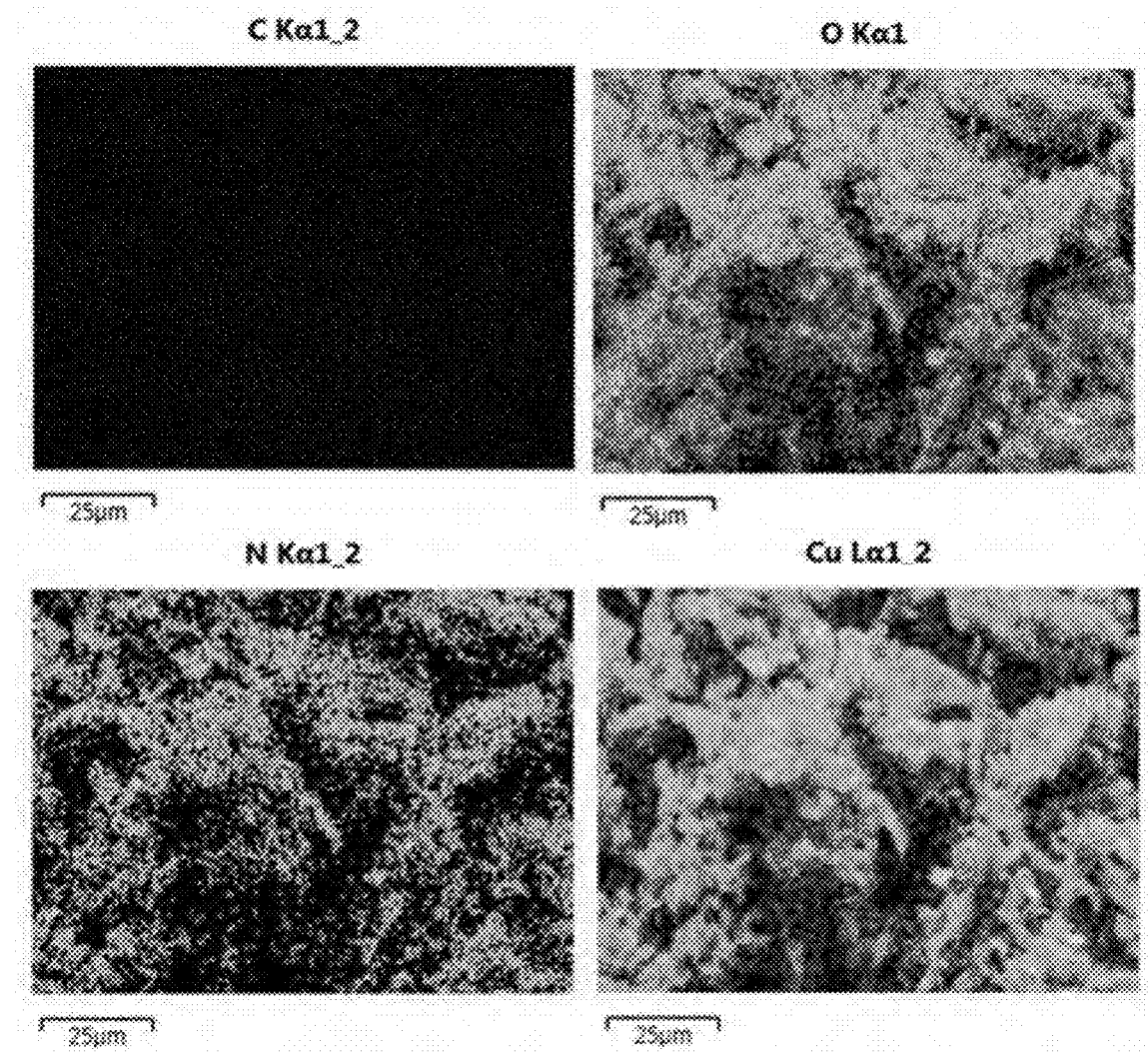
Figure 19A:
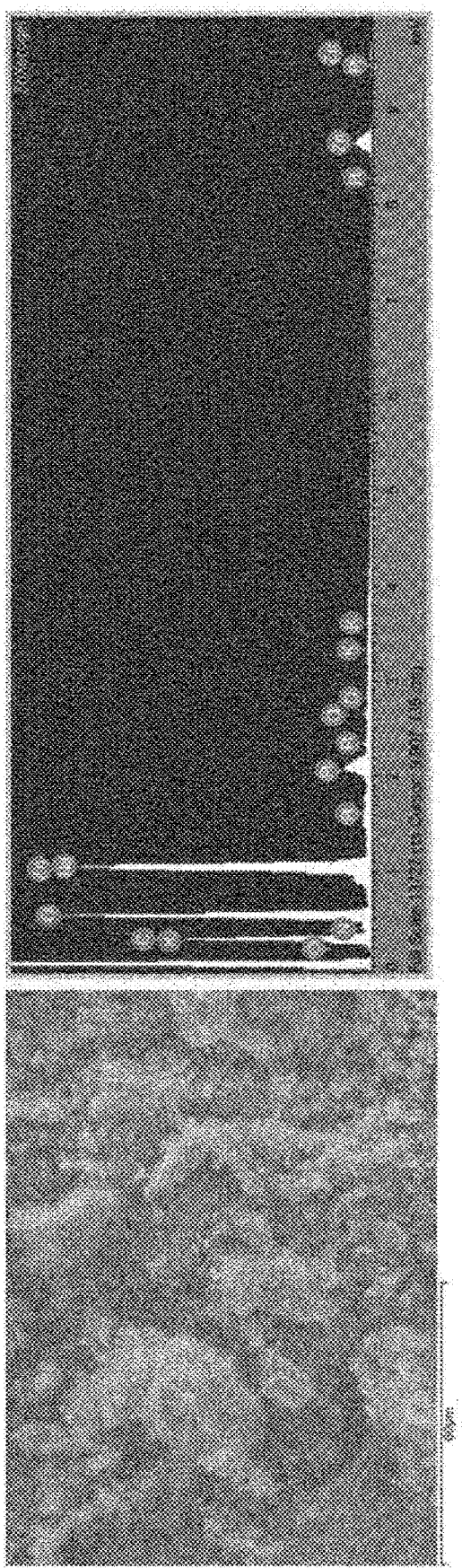
Figure 19B:
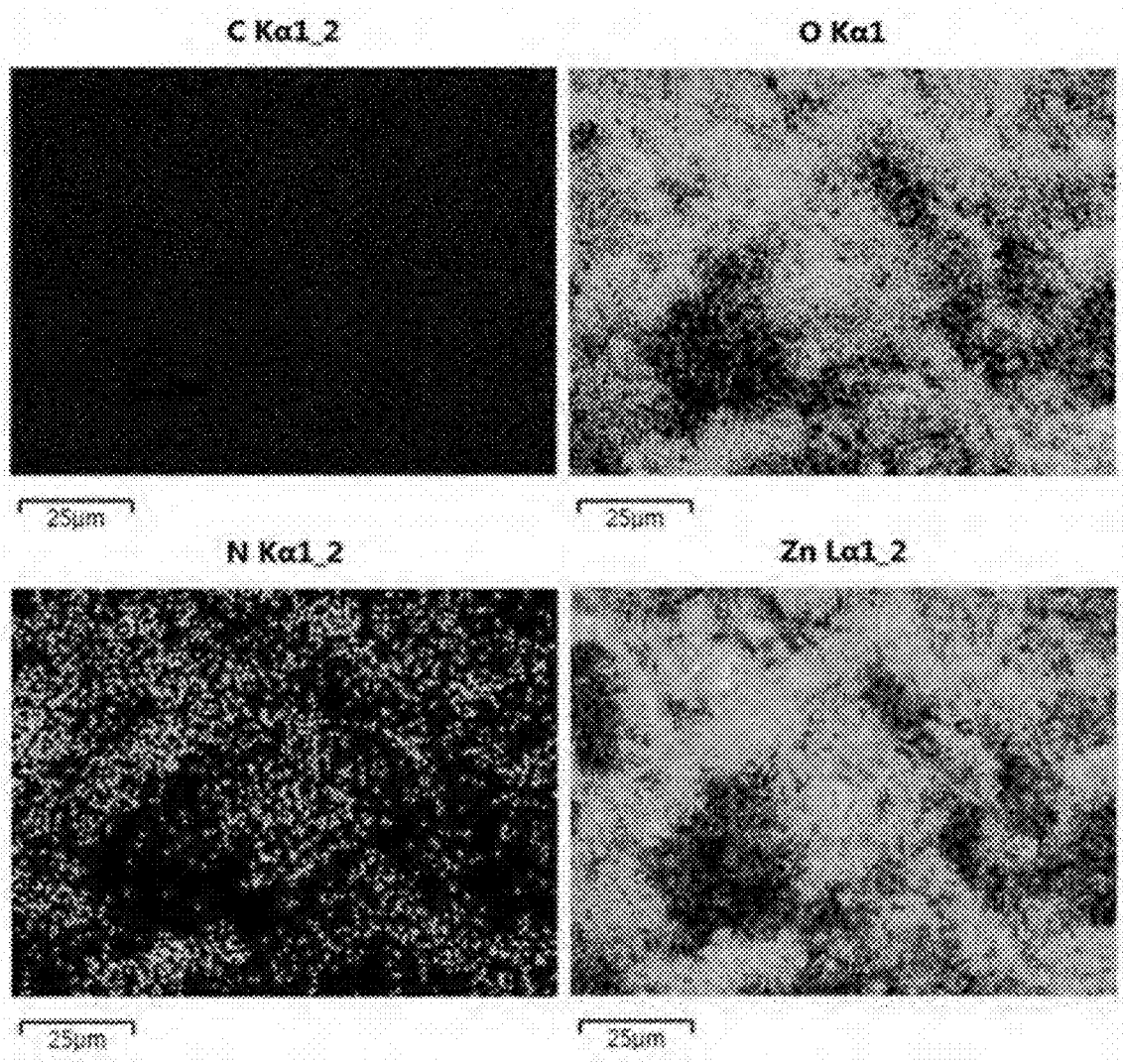
Figure 20A:
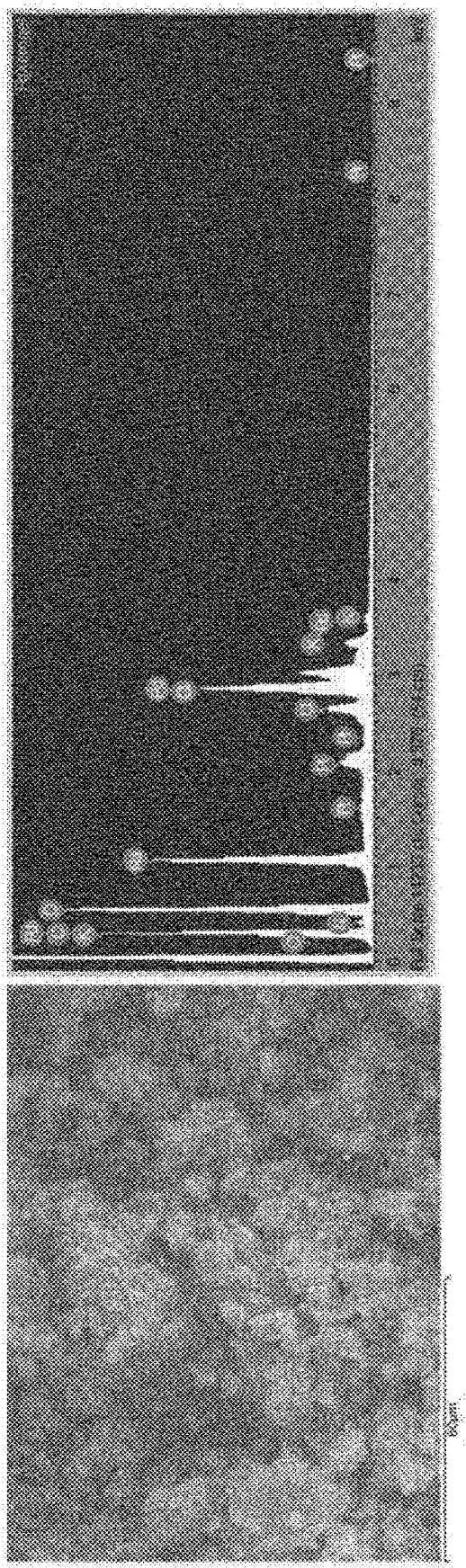
Figure 20B:
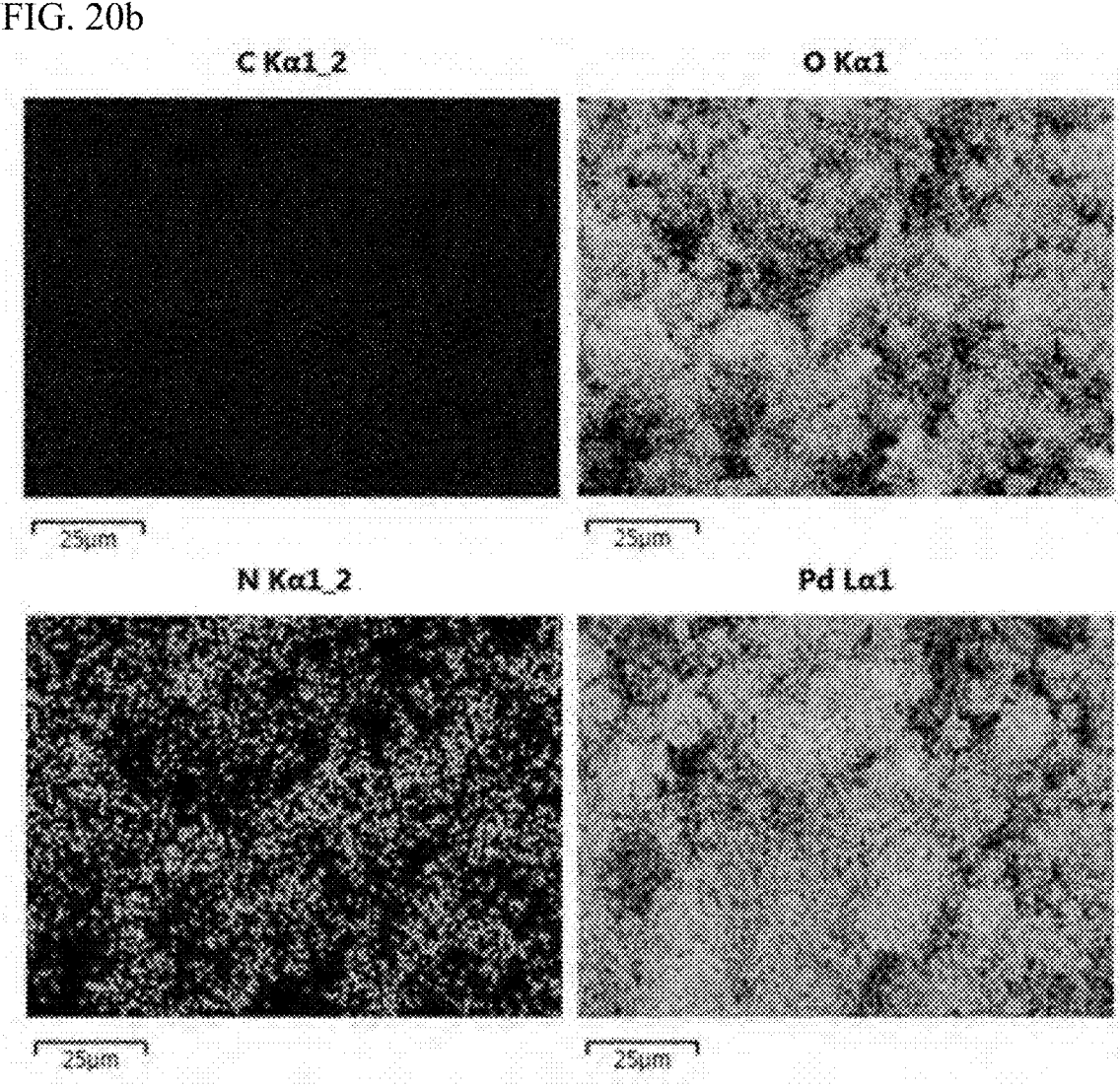
Figure 21A:
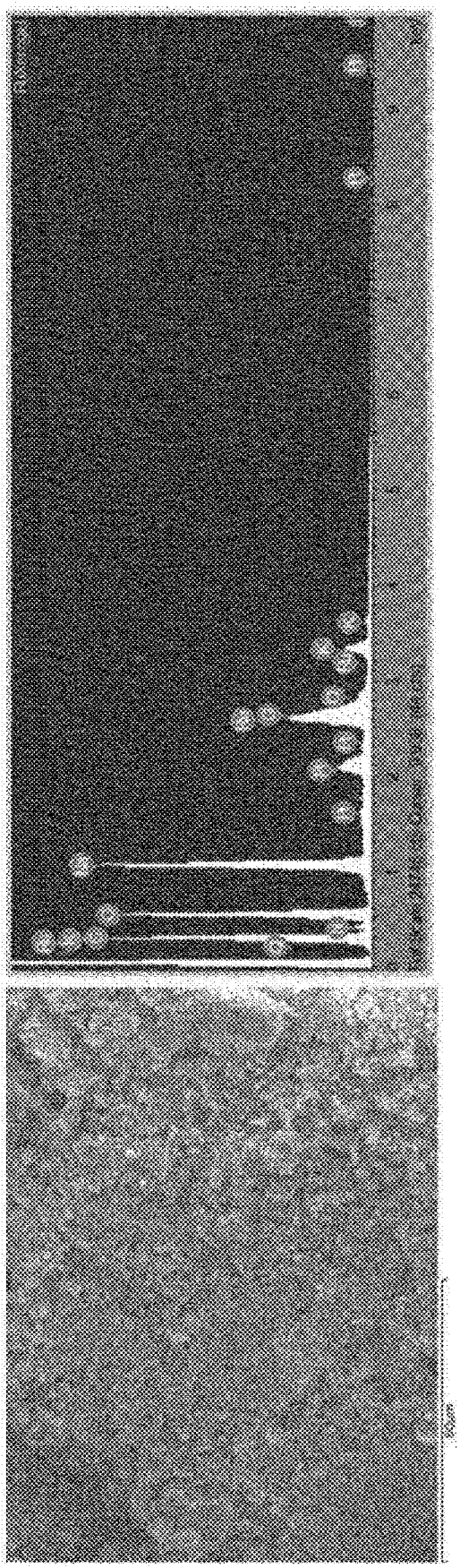
Figure 21B:
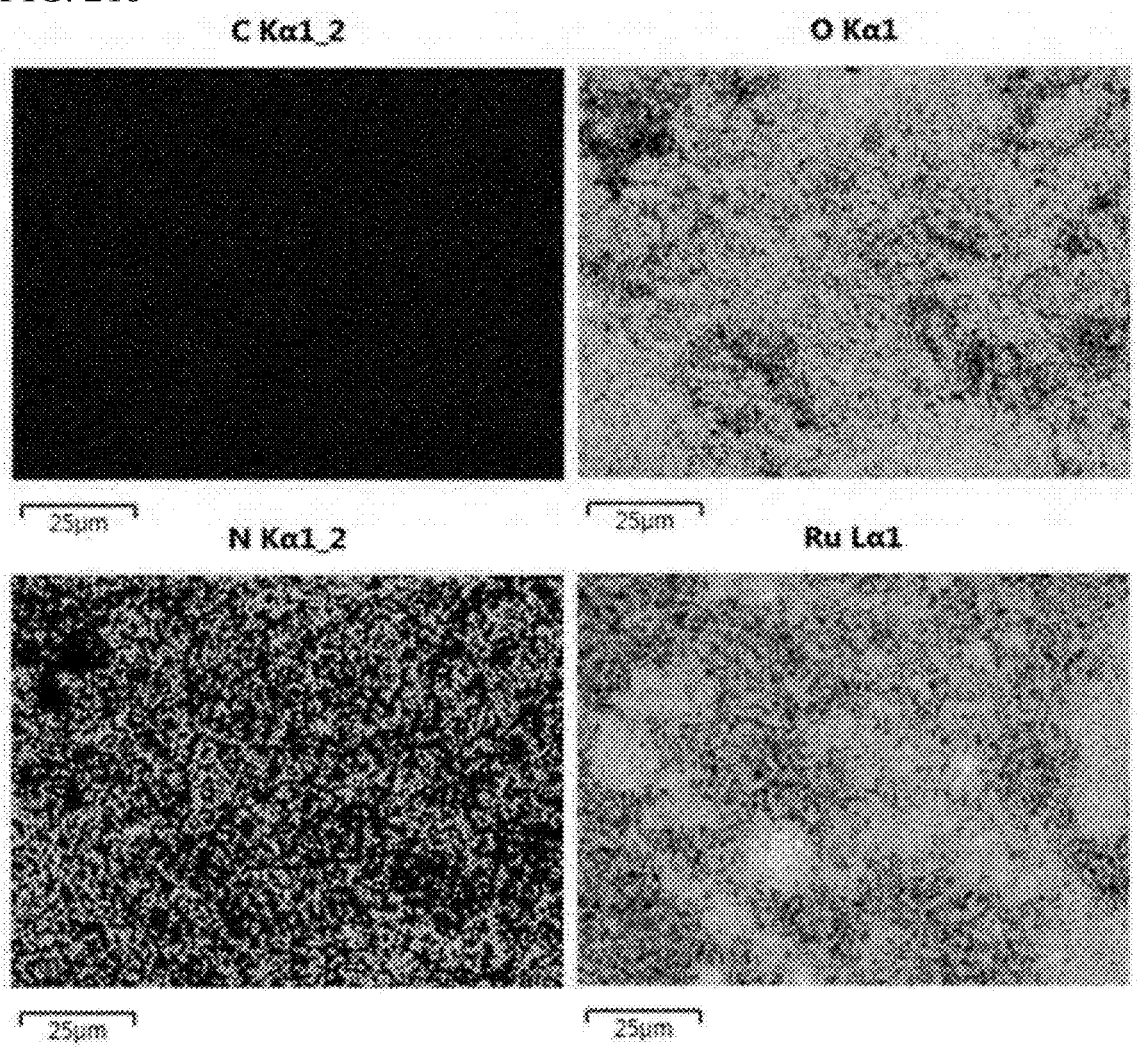
Figure 22A:
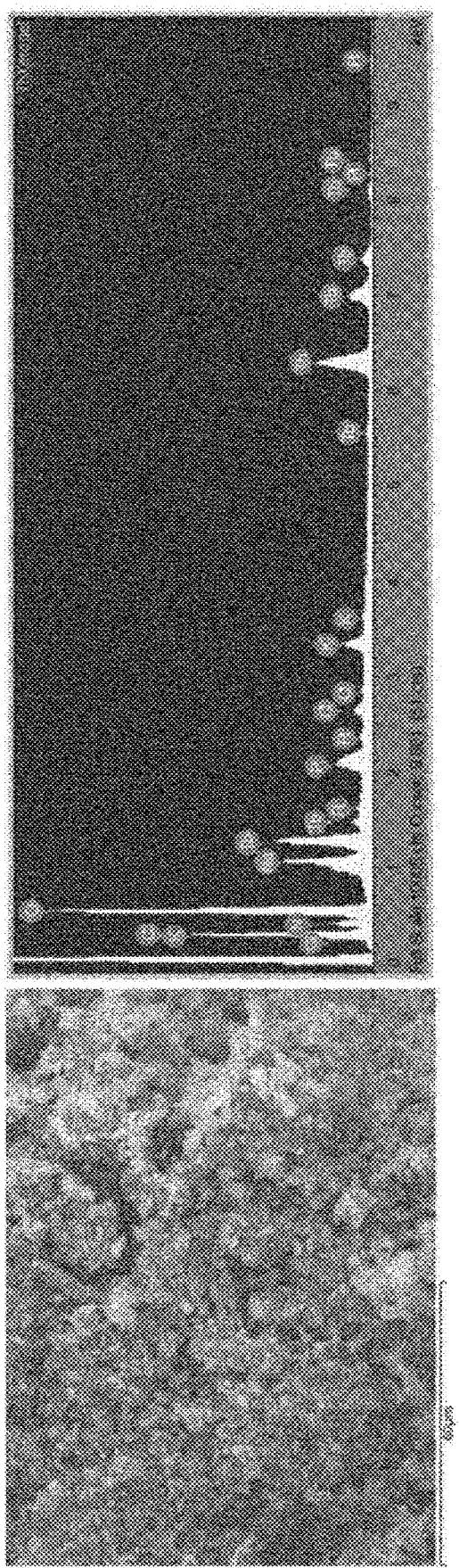
Figure 22B:
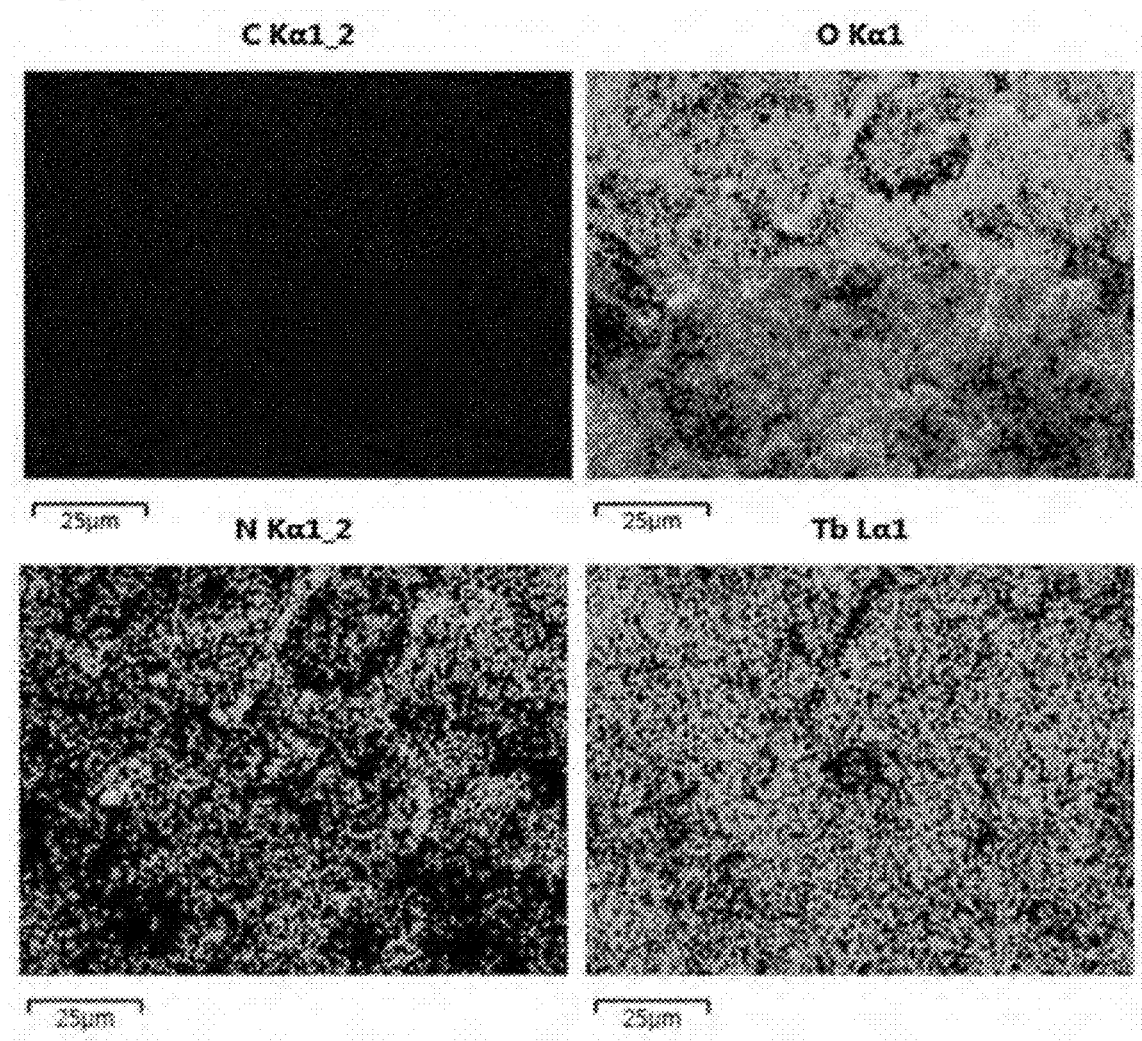
Figure 23A:
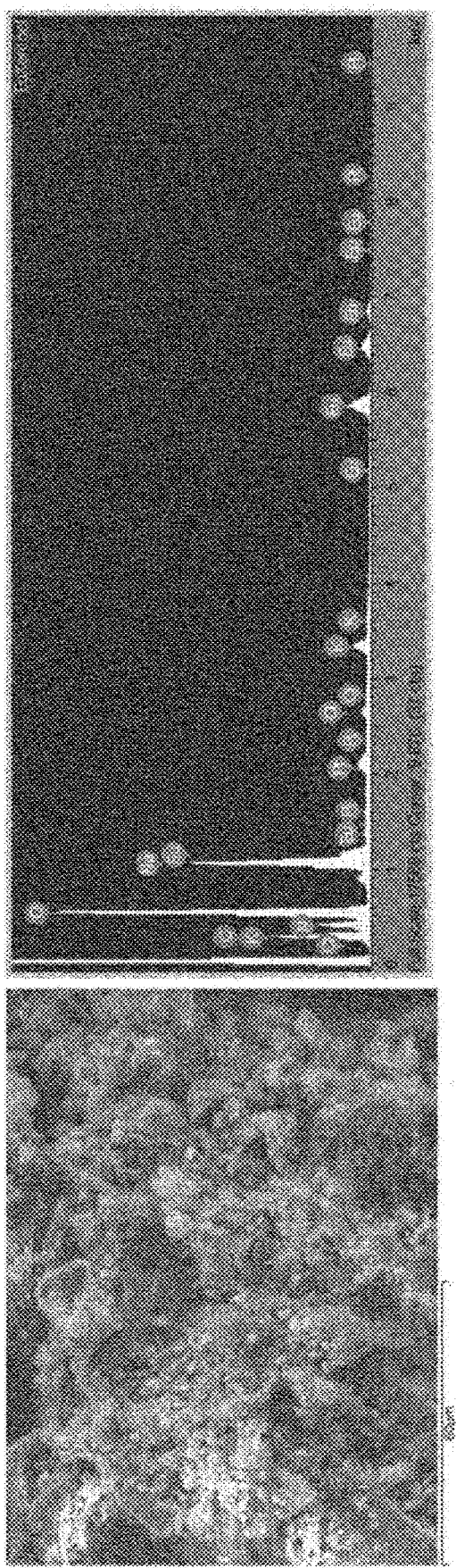
Figure 23B:
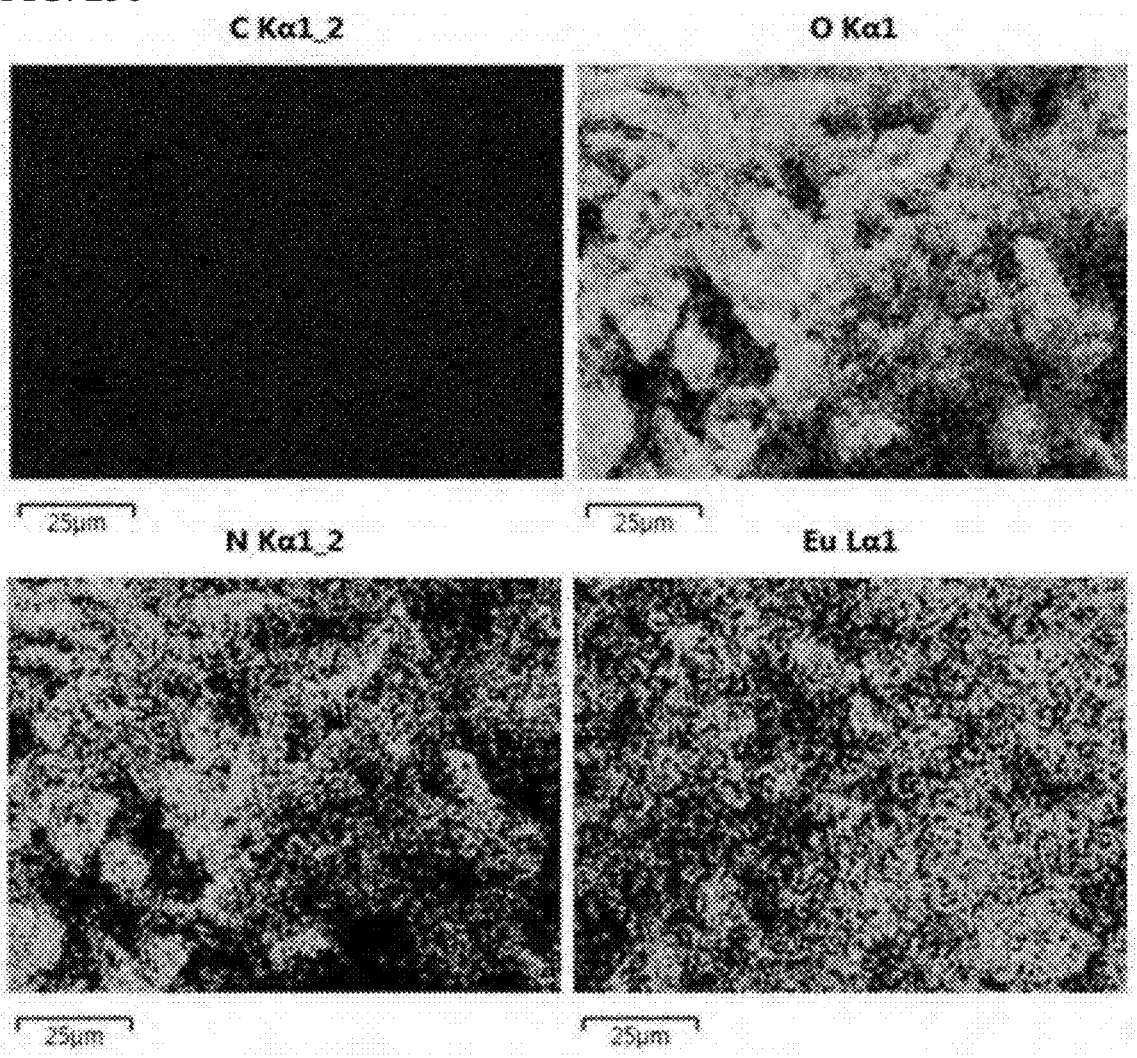

| | SEM image | Element distribution | SEM EDS component mapping |
|---|---|---|---|
| Xerogel (Fe xerogel) of Experimental Example 1-2 | FIG. 7 | FIG. 16a | FIG. 16b |
| Xerogel (Co xerogel) of Experimental Example 1-3 | FIG. 8 | FIG. 17a | FIG. 17b |
| Xerogel (Ni xerogel) of Experimental Example 1-4 | FIG. 9 | — | — |
| Xerogel (Cu xerogel) of Experimental Example 1-5 | FIG. 10 | FIG. 18a | FIG. 18b |
| Xerogel (Zn xerogel) of Experimental Example 1-6 | FIG. 11 | FIG. 19a | FIG. 19b |
| Xerogel (Pd xerogel) of Experimental Example 1-7 | FIG. 12 | FIG. 20a | FIG. 20b |
| Xerogel (Ru xerogel) of Experimental Example 1-8 | FIG. 13 | FIG. 21a | FIG. 21b |
| Xerogel (Tb xerogel) of Experimental Example 1-9 | FIG. 14 | FIG. 22a | FIG. 22b |
| Xerogel (Eu xerogel) of Experimental Example 1-10 | FIG. 15 | FIG. 23a | FIG. 23b |

The invention claimed is:

1. A metal-organic hybrid structure formed by the coordinate bonding of a compound represented by the following Chemical Formula 1 or a salt thereof with metal ions:

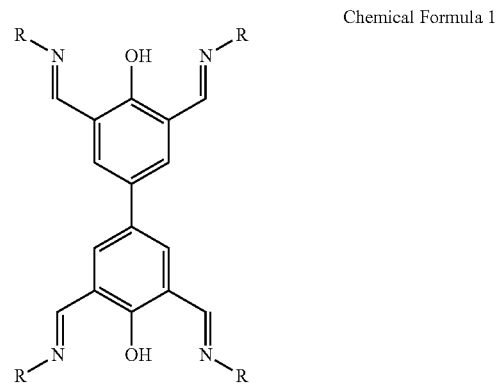

Chemical Formula 1 in the Chemical Formula 1,
R's are each independently —$R_1$, —NH—CO—$R_2$, or —NH—$R_3$,
$R_1$'s are each independently —OH, a $C_{6-60}$ aryl, methyl, ethyl, propyl, isopropyl, butyl, isobutyl, tert-butyl, pentyl, tert-pentyl, neopentyl, isopentyl, sec-pentyl, 3-pentyl, or an amino acid residue,
$R_2$'s are a $C_{1-10}$ alkyl, a $C_{6-60}$ aryl, or a $C_{4-60}$ heteroaryl containing one of N, O, and S, and
$R_3$'s are a $C_{1-10}$ alkyl, or a $C_{4-60}$ heteroaryl containing one of O and S.

2. The metal-organic hybrid structure according to claim 1, wherein $R_1$'s are each independently —OH, phenyl, naphthyl, or an amino acid residue selected from the group consisting of alanine, cysteine, aspartic acid, glutamic acid, phenylalanine, histidine, isoleucine, lysine, leucine, methionine, asparagine, pyrrolysine, glutamine, arginine, serine, threonine, selenocysteine, valine, tryptophan, and tyrosine.

3. The metal-organic hybrid structure according to claim 1, wherein $R_2$ is methyl, ethyl, propyl, isopropyl, butyl, isobutyl, tert-butyl, pentyl, tert-pentyl, neopentyl, isopentyl, sec-pentyl, 3-pentyl, hexyl, octyl, phenyl, naphthyl, or pyridinyl.

4. The metal-organic hybrid structure according to claim 1, wherein the compound represented by Chemical Formula 1 is a compound represented by one of the following Chemical Formulas 1-1 to 1-5:

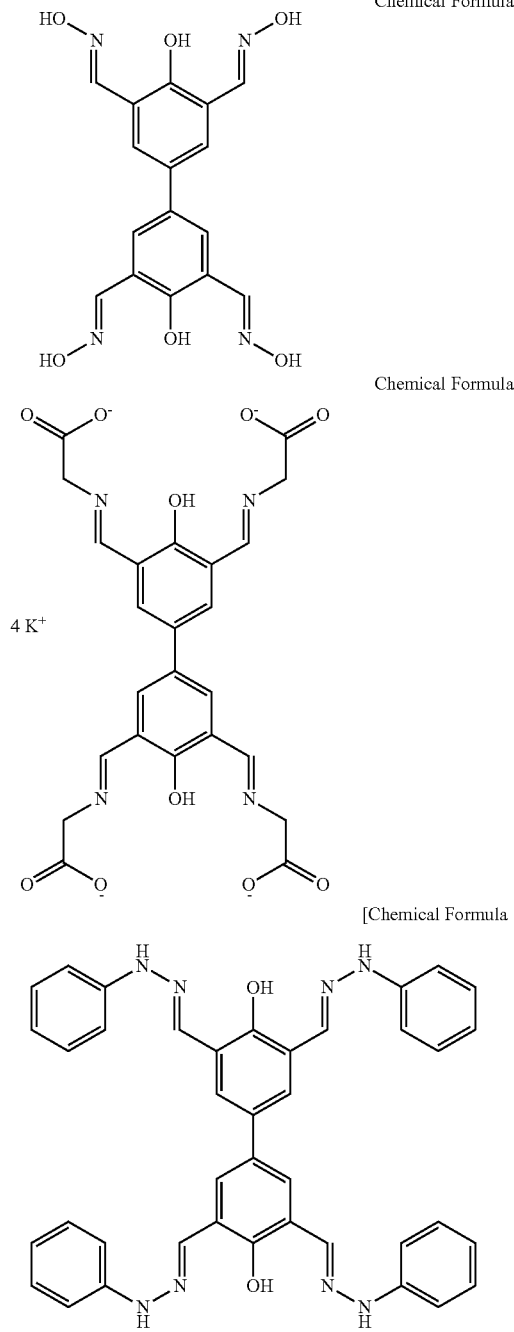

Chemical Formula 1-1

Chemical Formula 1-2

4 K⁺

[Chemical Formula 1-3]

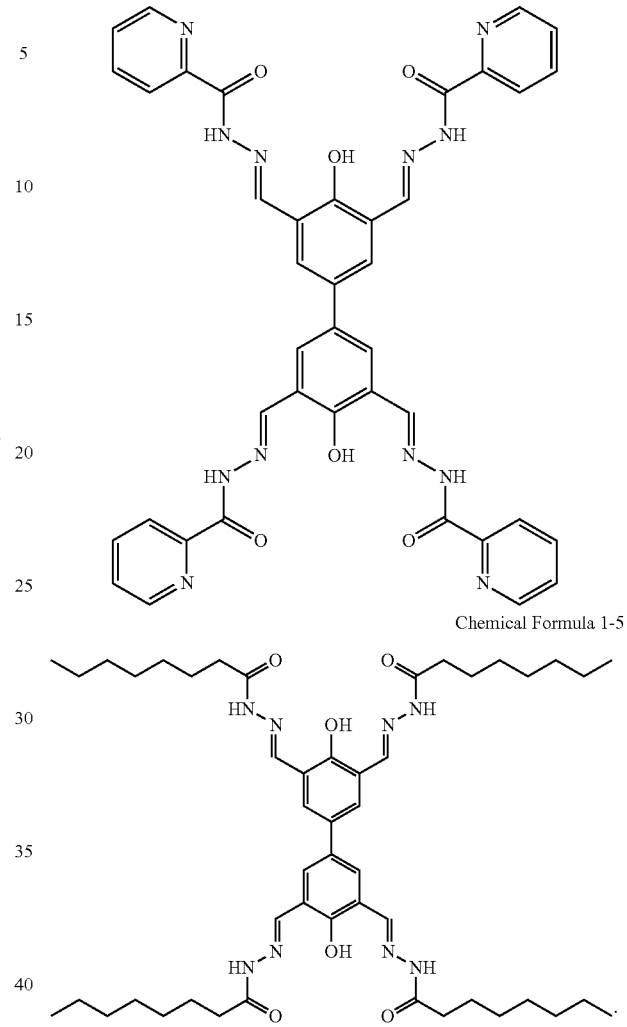

Chemical Formula 1-4

Chemical Formula 1-5

5. The metal-organic hybrid structure according to claim 1, wherein the metal of the metal ion is a Period 1 transition metal, a Period 2 transition metal, a Period 3 transition metal, or a lanthanide metal.

6. The metal-organic hybrid structure according to claim 1, wherein the metal of the metal ion is Ti, V, Mn, Fe, Co, Ni, Cu, Zn, Zr, Mo, Ru, Rh, Pd, Ag, Ir, Pt, Au, Tb, Eu, or Yb.

7. The metal-organic hybrid structure according to claim 1, wherein $R_3$ is methyl, ethyl, propyl, isopropyl, butyl, isobutyl, tert-butyl, pentyl, tert-pentyl, neopentyl, isopentyl, sec-pentyl, 3-pentyl, hexyl or octyl.

* * * * *

UNITED STATES PATENT AND TRADEMARK OFFICE
CERTIFICATE OF CORRECTION

| | |
|---|---|
| PATENT NO. | : 10,556,886 B2 |
| APPLICATION NO. | : 16/084959 |
| DATED | : February 11, 2020 |
| INVENTOR(S) | : Dongwhan Lee et al. |

It is certified that error appears in the above-identified patent and that said Letters Patent is hereby corrected as shown below:

In the Claims

At Column 14, Lines 66-67, to Column 16, Line 43, please replace Claim 4 with the following claim:
4. The metal-organic hybrid structure according to claim 1, wherein the compound represented by Chemical Formula 1 is a compound represented by one of the following Chemical Formulas 1-1 to 1-5:
Chemical Formula 1-1

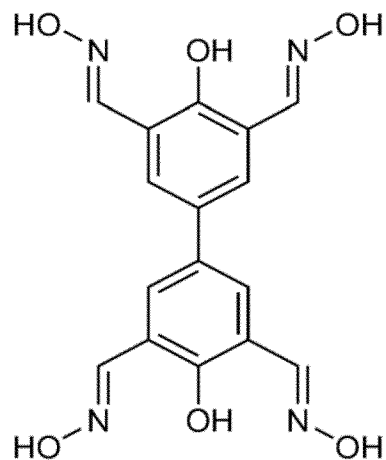

Signed and Sealed this
Twelfth Day of May, 2020

Andrei Iancu
*Director of the United States Patent and Trademark Office*

Chemical Formula 1-2
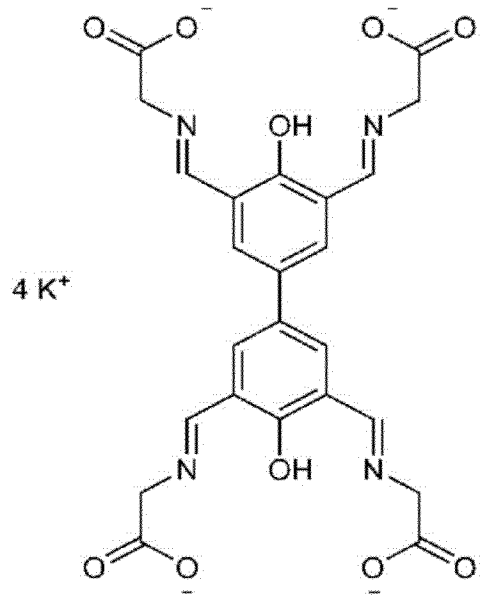
Chemical Formula 1-4
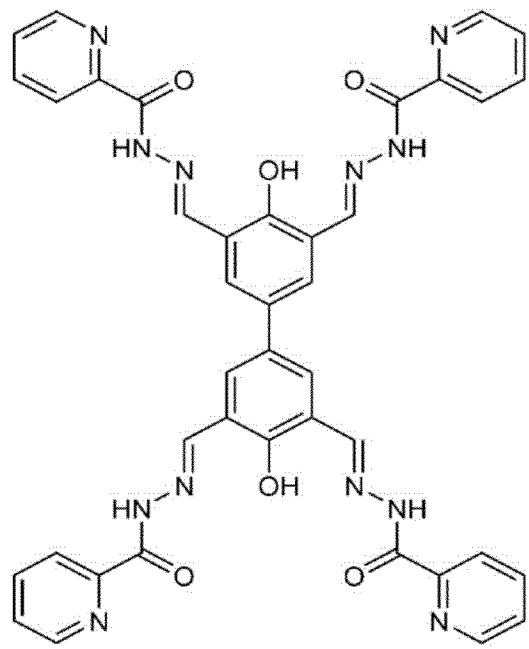

Chemical Formula 1-5
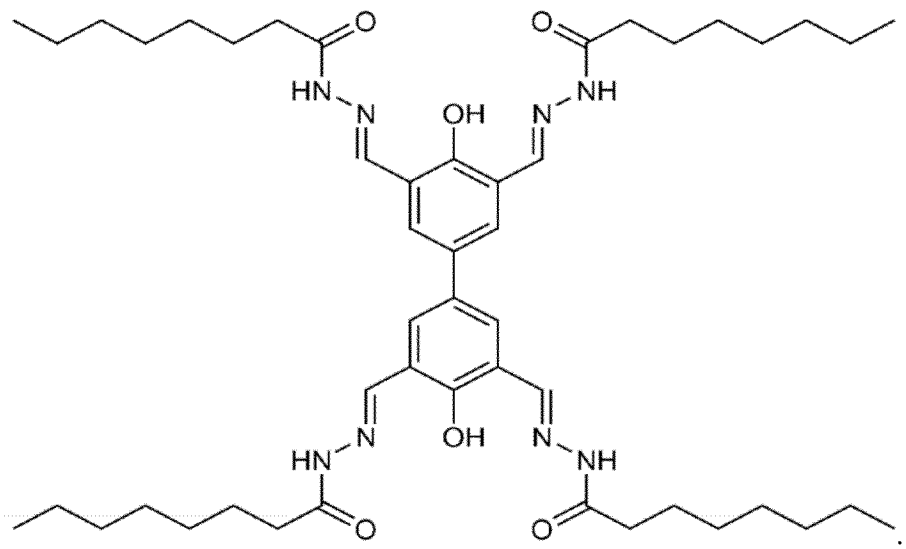
At Column 16, Lines 51-54, please replace Claim 7 with the following claim:
7. The metal-organic hybrid structure according to claim 1, wherein $R_3$ is methyl, ethyl, propyl, isopropyl, butyl, isobutyl, *tert*-butyl, pentyl, *tert*-pentyl, neopentyl, isopentyl, *sec*-pentyl, 3-pentyl, hexyl, or octyl.